(12) United States Patent
Blalock et al.

(10) Patent No.: US 9,275,630 B2
(45) Date of Patent: Mar. 1, 2016

(54) ULTRASOUND IMAGING BEAM-FORMER APPARATUS AND METHOD

(75) Inventors: Travis N Blalock, Charlottesville, VA (US); William F Walker, Earlysville, VA (US); John A Hossack, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 47 days.

(21) Appl. No.: 13/210,890

(22) Filed: Aug. 16, 2011

(65) Prior Publication Data

US 2012/0053460 A1    Mar. 1, 2012

Related U.S. Application Data

(63) Continuation of application No. 11/160,915, filed on Jul. 14, 2005, now abandoned, which is a continuation of application No. PCT/US2004/000887, filed on Jan. 14, 2004.

(Continued)

(51) Int. Cl.
  *A61B 8/14*    (2006.01)
  *G10K 11/34*   (2006.01)
  (Continued)

(52) U.S. Cl.
  CPC ............ *G10K 11/346* (2013.01); *A61B 8/4483* (2013.01); *G01S 7/5208* (2013.01);
  (Continued)

(58) Field of Classification Search
  CPC ...... A61B 8/00; A61B 8/4483; G10K 11/346; G01S 8/00; G01S 7/52028; G01S 7/52034; G01S 7/5208; G01S 15/8959; G01S 15/8995; G01S 15/8915
  See application file for complete search history.

(56) References Cited

U.S. PATENT DOCUMENTS

| 4,105,018 A | 8/1978 | Greenleaf et al. |
| 4,109,644 A | 8/1978 | Kojima |

(Continued)

FOREIGN PATENT DOCUMENTS

| DE | 19524505 A1 | 11/1996 |
| EP | 0173681 A1 | 5/1996 |

(Continued)

OTHER PUBLICATIONS

Ziomek et al., "Digital I/Q Demodulator", Proceedings of the 1995 Particle Accelerator Conference. vol. 4. p. 2663-2665.*

(Continued)

*Primary Examiner* — Long V Le
*Assistant Examiner* — Colin T Sakamoto
(74) *Attorney, Agent, or Firm* — Schwegman Lundberg & Woessner, P.A.

(57) ABSTRACT

In some illustrative embodiments, an incoming signal from a transducer in an ultrasound imaging beam-former apparatus is applied to an in-phase sample-and-hold and a quadrature sample-and-hold. The quadrature sample-and-hold may be clocked a quarter period behind the in-phase sample-and-hold. The output of the sample-and-holds are applied to in-phase and quadrature analog-to-digital converters. A magnitude calculator receives the in-phase and quadrature digital values, and outputs a magnitude. A phase calculator receives the in-phase and quadrature digital values, and outputs a phase. An apodizer applies a difference between an amplitude of the outgoing signal and the magnitude and applies a first illumination to a image point in substantial proportion to the difference, and a phase rotator applies a second illumination to the image point in substantial proportion to the phase.

29 Claims, 9 Drawing Sheets

Related U.S. Application Data

(60) Provisional application No. 60/440,020, filed on Jan. 14, 2003, provisional application No. 60/439,990, filed on Jan. 14, 2003, provisional application No. 60/440,262, filed on Jan. 15, 2003.

(51) Int. Cl.
  *A61B 8/00* (2006.01)
  *G01S 7/52* (2006.01)
  *G01S 15/89* (2006.01)

(52) U.S. Cl.
  CPC .............. *G01S15/8915* (2013.01); *A61B 8/00* (2013.01); *G01S 7/52028* (2013.01); *G01S 7/52034* (2013.01); *G01S 15/8959* (2013.01); *G01S 15/8995* (2013.01)

(56) References Cited

U.S. PATENT DOCUMENTS

| | | | |
|---|---|---|---|
| 4,275,461 A | 6/1981 | Sternick et al. | |
| 4,338,948 A | 7/1982 | Perez-Mendez et al. | |
| 4,573,477 A | 3/1986 | Namekawa et al. | |
| 4,640,291 A | 2/1987 | t Hoen | |
| 4,671,293 A | 6/1987 | Shaulov | |
| 4,694,434 A | 9/1987 | von Ramm et al. | |
| 4,817,614 A | 4/1989 | Hassler et al. | |
| 4,867,167 A | 9/1989 | Magnin | |
| 4,870,867 A | 10/1989 | Shaulov | |
| 4,949,310 A | 8/1990 | Smith et al. | |
| 5,014,712 A | 5/1991 | O'donnell | |
| 5,027,821 A | 7/1991 | Hirama et al. | |
| 5,095,890 A | 3/1992 | Houghton et al. | |
| 5,105,814 A | 4/1992 | Drukarev et al. | |
| 5,119,342 A | 6/1992 | Harrison, Jr. et al. | |
| 5,186,177 A | 2/1993 | O'Donnell et al. | |
| 5,230,340 A * | 7/1993 | Rhyne | 600/447 |
| 5,268,876 A | 12/1993 | Rachlin | |
| 5,331,964 A | 7/1994 | Trahey et al. | |
| 5,454,809 A | 10/1995 | Janssen et al. | |
| 5,469,851 A | 11/1995 | Lipschutz | |
| 5,471,990 A | 12/1995 | Thirsk | |
| 5,487,387 A | 1/1996 | Trahey et al. | |
| 5,531,117 A | 7/1996 | Fortes | |
| 5,546,807 A | 8/1996 | Oxaal et al. | |
| 5,566,675 A | 10/1996 | Li et al. | |
| 5,590,658 A | 1/1997 | Chiang et al. | |
| 5,626,576 A | 5/1997 | Janssen | |
| 5,632,277 A | 5/1997 | Chapman et al. | |
| 5,673,699 A * | 10/1997 | Trahey et al. | 600/447 |
| 5,684,484 A | 11/1997 | Suzuki | |
| 5,707,845 A | 1/1998 | Ueyama et al. | |
| 5,722,412 A | 3/1998 | Pflugrath | |
| 5,793,701 A | 8/1998 | Wright et al. | |
| 5,797,845 A | 8/1998 | Barabash et al. | |
| 5,801,657 A * | 9/1998 | Fowler et al. | 341/155 |
| 5,817,024 A | 10/1998 | Ogle et al. | |
| 5,882,307 A | 3/1999 | Wright et al. | |
| 5,893,363 A | 4/1999 | Little et al. | |
| 5,924,993 A | 7/1999 | Hadjicostis et al. | |
| 5,947,905 A | 9/1999 | Hadjicostis et al. | |
| 5,997,477 A | 12/1999 | Sehgal | |
| 5,997,479 A | 12/1999 | Savord et al. | |
| 5,999,747 A | 12/1999 | Imura et al. | |
| 6,013,032 A | 1/2000 | Savord | |
| 6,016,285 A | 1/2000 | Wright | |
| 6,027,447 A | 2/2000 | Li et al. | |
| 6,048,316 A | 4/2000 | Zhao et al. | |
| 6,059,730 A | 5/2000 | Miwa et al. | |
| 6,063,033 A | 5/2000 | Haider et al. | |
| 6,068,597 A | 5/2000 | Lin | |
| 6,071,240 A | 6/2000 | Hall et al. | |
| 6,074,346 A | 6/2000 | Oppelt | |
| 6,120,450 A | 9/2000 | Li et al. | |
| 6,126,602 A | 10/2000 | Savord et al. | |
| 6,135,961 A | 10/2000 | Pflugrath et al. | |
| 6,142,946 A | 11/2000 | Hwang et al. | |
| 6,179,780 B1 | 1/2001 | Hossack et al. | |
| 6,203,498 B1 | 3/2001 | Bunce et al. | |
| 6,251,074 B1 | 6/2001 | Averkiou et al. | |
| 6,276,211 B1 | 8/2001 | Smith | |
| 6,380,766 B2 | 4/2002 | Savord et al. | |
| 6,383,139 B1 | 5/2002 | Hwang et al. | |
| 6,416,475 B1 | 7/2002 | Hwang et al. | |
| 6,423,002 B1 | 7/2002 | Hossack | |
| 6,443,896 B1 | 9/2002 | Detmer | |
| 6,443,900 B2 | 9/2002 | Adachi et al. | |
| 6,450,960 B1 | 9/2002 | Rather et al. | |
| 6,471,651 B1 | 10/2002 | Hwang et al. | |
| 6,482,160 B1 | 11/2002 | Stergiopoulos et al. | |
| 6,491,634 B1 | 12/2002 | Leavitt et al. | |
| 6,537,219 B2 | 3/2003 | Poland et al. | |
| 6,540,677 B1 | 4/2003 | Angelsen et al. | |
| 6,572,547 B2 | 6/2003 | Miller et al. | |
| 6,582,372 B2 | 6/2003 | Poland | |
| 6,641,534 B2 | 11/2003 | Smith et al. | |
| 6,650,264 B1 * | 11/2003 | Chan et al. | 341/143 |
| 6,669,641 B2 | 12/2003 | Poland et al. | |
| 6,692,439 B1 | 2/2004 | Walker et al. | |
| 7,064,700 B1 | 6/2006 | Garrity et al. | |
| 7,402,136 B2 | 7/2008 | Hossack et al. | |
| 2002/0144549 A1 | 10/2002 | Yao | |
| 2004/0000841 A1 | 1/2004 | Phelps et al. | |
| 2005/0154300 A1 | 7/2005 | Wodnicki et al. | |
| 2007/0016022 A1 | 1/2007 | Blalock et al. | |
| 2007/0016044 A1 | 1/2007 | Blalock et al. | |

FOREIGN PATENT DOCUMENTS

| | | |
|---|---|---|
| EP | 0713681 B1 | 7/2007 |
| WO | WO-2004064619 A2 | 8/2004 |
| WO | WO-2004064619 A3 | 8/2004 |
| WO | WO-2004064620 A2 | 8/2004 |
| WO | WO-2004064620 A3 | 8/2004 |
| WO | WO-2004065978 A2 | 8/2004 |
| WO | WO-2004065978 A3 | 8/2004 |

OTHER PUBLICATIONS

Maxim Integrated "Multiply Your Sampling Rate with Time-Interleaved Data Converters" Tutorial 989, Mar. 1, 2001.*

"U.S. Appl. No. 10/542,242, Non Final Office Action mailed Dec. 1, 2006", 8 pgs.

"U.S. Appl. No. 10/542,242, Notice of Allowance mailed Jun. 15, 2007", 5 pgs.

"U.S. Appl. No. 10/542,242, Preliminary Amendment filed Jul. 14, 2005", 3 pgs.

"U.S. Appl. No. 10/542,242, Response filed Apr. 2, 2007 to Non Final Office Action mailed Dec. 1, 2006", 10 pgs.

"U.S. Appl. No. 11/160,914, Final Office Action mailed Sep. 14, 2011", 10 pgs.

"U.S. Appl. No. 11/160,914, Final Office Action mailed Oct. 31, 2013", 16 pgs.

"U.S. Appl. No. 11/160,914, Non Final Office Action mailed Jan. 21, 2010", 15 pgs.

"U.S. Appl. No. 11/160,914, Non Final Office Action mailed Mar. 13, 2013", 15 pgs.

"U.S. Appl. No. 11/160,914, Non Final Office Action mailed Dec. 17, 2010", 12 pgs.

"U.S. Appl. No. 11/160,914, Pre-Appeal Brief filed Apr. 3, 2014", 5 pgs.

"U.S. Appl. No. 11/160,914, Response filed Mar. 13, 2012 to Final Office Action mailed Sep. 14, 2011", 17 pgs.

"U.S. Appl. No. 11/160,914, Response filed Jun. 17, 2011 to Non Final Office Action mailed Dec. 17, 2010", 20 pgs.

"U.S. Appl. No. 11/160,914, Response filed Jul. 21, 2010 to Non Final Office Action mailed Jan. 21, 2010", 17 pgs.

"U.S. Appl. No. 11/160,914, Response filed Aug. 13, 2013 to Non Final Office Action mailed Mar. 13, 2013", 20 pgs.

"U.S. Appl. No. 11/160,914, Supplemental Amendment filed Jul. 12, 2010", 3 pgs.

(56) References Cited

OTHER PUBLICATIONS

"U.S. Appl. No. 11/160,915, Non Final Office Action mailed Feb. 17, 2011", 11 pgs.
"U.S. Appl. No. 11/160,915, Non Final Office Action mailed Jun. 28, 2010", 8 pgs.
"U.S. Appl. No. 11/160,915, Response filed Feb. 12, 2010 to Restriction Requirement mailed Jan. 12, 2010", 15 pgs.
"U.S. Appl. No. 11/160,915, Response filed Oct. 28, 2010 to Non Final Office Action mailed Jun. 28, 2010", 11 pgs.
"U.S. Appl. No. 11/160,915, Restriction Requirement mailed Jan. 12, 2010", 6 pgs.
"Canadian Application Serial No. 2,513,447, Office Action mailed Apr. 9, 2014", 3 pgs.
"European Application Serial No. 04702168.8, European Search Report mailed May 27, 2009", 4 pgs.
"European Application Serial No. 04702168.8, Office Action mailed Aug. 10, 2011", 4 pgs.
"European Application Serial No. 04702168.8, Office Action mailed Sep. 3, 2009", 6 pgs.
"European Application Serial No. 04702168.8, Response filed Apr. 13, 2010 to Office Action mailed Sep. 3, 2009", 91 pgs.
"European Application Serial No. 04702168.8, Response filed Sep. 12, 2011 to Office Action mailed Aug. 10, 2011", 13 pgs.
"European Application Serial No. 04702545.7, European Search Report mailed Jun. 5, 2007", 3 pgs.
"European Application Serial No. 04702545.7, Office Action mailed Jul. 13, 2010", 8 pgs.
"European Application Serial No. 04702545.7, Office Action mailed Sep. 26, 2007", 4 pgs.
"European Application Serial No. 04702545.7, Response filed Apr. 4, 2008 to Office Action mailed Sep. 26, 2007", 28 pgs.
"International Application Serial No. PCT/US2004/000887, International Preliminary Report on Patentability mailed Jul. 15, 2005", 4 pgs.
"International Application Serial No. PCT/US2004/000887, Written Opinion mailed Nov. 1, 2004", 3 pgs.
"International Application Serial No. PCT/US2004/000888, International Preliminary Report on Patentability mailed Jul. 15, 2005", 4 pgs.
"International Application Serial No. PCT/US2004/000888, Written Opinion mailed Sep. 7, 2004", 3 pgs.
"International Application Serial No. PCT/US2004/001002, International Preliminary Report on Patentability mailed Nov. 21, 2008", 6 pgs.
"International Application Serial No. PCT/US2004/001002, Written Opinion mailed Aug. 20, 2004", 5 pgs.
"Philips' New 3D Technology Puts the Beating Heart in Physicians' Hands", Philips Medical Systems Press Release. Business Wire, (Nov. 15, 2002), 4 pgs.
Anderson, et al., "A Handle-Mounted Multiplexing Pre-amplifier for Synthetic Receive Aperture Imagining", 19th Annual Symposium on Ultrasonic Imagine and Tissue Characterization vol. 16, (1994), 55.
Blalock, T. N., et al., "A 1.5 GOPS Analog CMOS Array Processor with Integrated Optical Image Acquisition for Position Encoding Applications", Proc. of the Int. Sym. on VLSI Circuits, (1998), 204-205.
Blalock, T. N, et al., "True Color 1024×768 Microdisplay with Analog In-Pixel Pulse Width Modulation and Retinal Averaging Offset Correction", IEEE Journal of Solid-State Circuits 36(5), (May 2001), 838-845.
Campbell, J A, et al., "Measurements of Calf liver ultrasonic differential and total scattering cross sections", J. Acoust. Soc. Am., vol. 45, No. 2, (Feb. 1994), 603-611.
Davidsen, et al., "Sparse Geometrics for two dimensional array transducers in volumetric imaging", IEEE Ultrasonics symposium, (1993), 1091-1094.
Davros, W J, et al., "Frequency-dependent angular scattering of Ultrasound by Tissue-Mimicking materials and Excised tissue", J. Acoust. Soc. Am., vol. 80, No. 1, (Jul. 1986), 229-237.

Emery, Charles, et al., "Ultrasonic imaging using a 5-MHz multilayer/single-layer hybrid array for increased signal-to-noise ratio", IEEE Transactions on Ultrasonics, Ferroelectrics, and Frequency Control 46(5), (1999), 1101-1119.
Fabian, C. M, et al., "Development of a Parellel Acquisition System for Ultrasound Research", Proc. SPIE. vol. 4325. Medical Imaging: Ultrasonic Imaging and Signal Processing, (2001), 54-62.
Foster, et al., "A digital annular array prototype scanner for realtime ultrasound imaging", Ultrasound in Medicine and Biology 15(7), (1989), 661-672.
Fritsch, et al., "Beamforming with a reduced sampling rate", Ultrasonics, IPC Science and Technology Press ltd. 40(1-8), (2002), 599-604.
Fuller, et al., "A Portable, Low-Cost, Highly Integrated, 3D Medical Ultrasound System", IEEE Ultrasonics Symposium vol. 1, (2003), 38-41.
Jensen, J Arendt, et al., "Calculation of Pressure Fields from Arbitrarily Shaped, Apodized, and Excited Ultrasound Transducers", IEEE Transactions on Ultrasonics, Ferroelectrics and Frequency Control vol. 39, No. 2, (Mar. 1992), 262-267.
Kasai, Chihiro, et al., "Real-Time Two-Dimensional Blood Flow Imaging Using an Autocorrelation Technique", IEEE, vol. SU-32, No. 3, (May 1985), pp. 458-464.
Kim, Joo Han, et al., "Pipelined sampled-delay focusing in ultrasound imaging systems", Ultrasonic Imaging Dynamedia inc 9(2), (1987), 75-91.
Kleinfelder, et al., "A 10k Frames per Second 0.18 Micron CMOS Digital Pixel Sensor with Pixel-Level Memory", Proc. of ISSCC Solid-State Circuits Conference, (2001), 88-89 and 435-436.
Kwon, O, et al., "A Novel Double Slope Analog-toDigital Converter for a High Quality 640×480 CMOS Imaging System", Proc. of the 6th Int. Conf on VLSI and CAD, (1999), 335-338.
Lacefield, J C, et al., "Angular Scatter Ultrasound Imaging using Separated Arrays", Thesis, Duke University, (1999), 209 pgs.
Lee, W, et al., "Real Time Three Dimensional Intracardiac Echocardiography for Guidance of Cardiac Interventional Procedures", Presented at IEEE Ultrasonics Symposium, (2001), 1307-1310.
Light, E, et al., "Real-time three-dimensional intracardiac echocardiography", Ultrasound in Medicine and Biology 27(9), (2001), 1173-1183.
Light, E, et al., "Two dimensional arrays for real time volumetric and intracardiac imaging with simultaneous electrocardiogram", Presented at IEEE Ultrasonics Symposium, (2000), 1195-1198.
Light, E, "Update of two dimensional arrays for real time volumetric and real time intracardiac imaging", Presented at IEEE Ultrasonics Symposium, (1999), 1217-1220.
Lockwood, et al., "Optimizing the radiation Pattern of Sparse Periodic Linear Arrays", IEEE Transactions on Ultrasonics, Ferroelectrics and Frequency Control 43(1), (1996), 7-14.
Magnin, et al., "Frequency compounding for speckle contrast reduction in phased array images", Ultrasonic Imaging 4, (1982), 267-281.
Mann, J. A, et al., "A Constrained Adaptive Beamformer for Medical Ultrasound", 2002 IEEE Ultrasonics Symposium, 2002. Proceedings, vol. 2, (2002), 1807-1810.
Melton, et al., "A-mode speckle reduction with compound frequencies and compund bandwidths", Ultrasonic Imagining 6, (1984), 159-173.
Mills, D, et al., "Multi-Layered PZT/polymer composites to increase signal-to-noise ratio and resolution for medical ultrasound transducers. II. Thick film technology", IEEE Transactions on Ultrasonics, Ferroelectrics, and Frequency Control 49(7), (2002), 1005-1014.
Nassiri, D K, et al., "The Use of Angular Acoustic Scattering Measurements to Estimate Structural parameters of Human and Animal Tissues", J. Acoust. Soc. Am., vol. 79, No. 6, (Jun. 1986), 2048-2054.
Ng, Gary, et al., "A Speckle Target Adaptive Imaging Technique in the Presence of Distributed Aberrations", IEEE Transactions on Ultrasonics, Ferroelectrics, and Frequency Control, vol. 44, No. 1, (Jan. 1997), 140-151.
O'Donnell, et al., "Optimum displacement for compound image generation in medical ultrasound", IEEE Transactions on Ultrasonics, Ferroelectrics, and Frequency Control 35(4), (1988), 470-476.

(56) References Cited

OTHER PUBLICATIONS

Plummer, et al., "Two-dimensional Transmit/Receive Ceramic Piezoelectric Arrays: Construction and Performance", IEEE Transactions on Sonics and Ultrasonics vol. SU-25(5), (1978), 273-280.

Rachlin, Daniel, et al., "Direct Estimation of Aberrating Delays in Pulse-echo Imaging Systems", J. Acoust. Soc. Am., vol. 88, No. 1, (Jul. 1990), 191-198.

Ranganathan, et al., "A Novel Beamformer Design Method for Medical Ultrasound. Part II: Simulation Results", IEEE Transactions on Ultrasonics, Ferroelectrics, and Frequency Control 50(1), (2003), 25-39.

Ranganathan, et al., "A Novel Beamformer Design Method for Medical Ultrasound: Part I: Theory", IEEE Transactions on Ultrasonics, Ferroelectrics, and Frequency Control 50(1), (Jan. 2003), 15-24.

Ranganathan, K., et al., "Direct sampled I/Q beamforming for compact and very low-cost ultrasound imaging", IEEE Trans Ultrason Ferroelectr Freq Control., 51(9), (Sep. 2004), 1082-94.

Robinson, Marshal T, et al., "Real-Time Angular Scatter Imaging System for Improved Tissue Contrast in Diagnostic Ultrasound Images", IEEE Transactions on Ultrasonics and Frequency Control, vol. 41, No. 1, (Jan. 1994), 44-52.

Trahey, et al., "A quantitative approach to speckle reduction via frequency compounding", Ultrason. Imag. 8, (1986), 151-164.

Trahey, et al., "Speckle pattern correlation with lateral aperture translation: experimental results and implications for spatial compounding", IEEE Transactions on Ultrasonics, Ferroelectrics, and Frequency Control vol. UFFC-33(3), (May 1986), 257-264.

Von Ramm, et al., "Real time volumetric ultrasound imagining system", Journal of Digital Imaging 3(4), (1990), 261-266.

Von Ramm, Olaf T, et al., "High-speed ultrasound volumetric imaging system. II. Parallel processing and image display", IEEE Transactions on Ultrasounics, Ferroelectrics, and Frequency Control 38(2), (Mar. 1991), 109-115.

Walker, W F, et al., "Speckle Coherence and implications for adaptive imaging", J. Acoust. Soc. Am., vol. 101, No. 4, (Apr. 1994), 1847-1858.

Walker, W F, et al., "The Application of K-Space in Medical Ultrasound", IEEE Ultrasonics Symposium, (1995), 1379-1383.

Walker, William, "A New Class of Aperture Domain Flow Estimation Algorithms", Proc. IEEE Ultrason. Symp. 2, (1997), 1227-1231.

Yang, D.X.D, et al., "A Nyquist-Rate Pixel-Level ADC for CMOS Image Sensors", IEEE Journal of Solid-State Circuits 34(3), (Mar. 1999), 348-356.

"U.S. Appl. No. 11/160,914, Decision on Pre-Appeal Brief Request mailed May 22, 2014", 2 pgs.

"U.S. Appl. No. 11/160,914, Non Final Office Action mailed Jan. 29, 2015", 21 pgs.

"U.S. Appl. No. 11/160,914, Response filed Dec. 1, 2014 to Final Office Action mailed Oct. 31, 2014", 17 pgs.

"Canadian Application Serial No. 2,513,447, Response filed Oct. 9, 2014 to Office Action mailed Apr. 9, 2014", 24 pgs.

Li, Yue, et al., "Phase Aberration Correction Algorithm Using Near-Field Signal Redundancy Method: Algorithm", Ultrasonic Imaging, vol. 17, Abstract, (1995), p. 64.

* cited by examiner

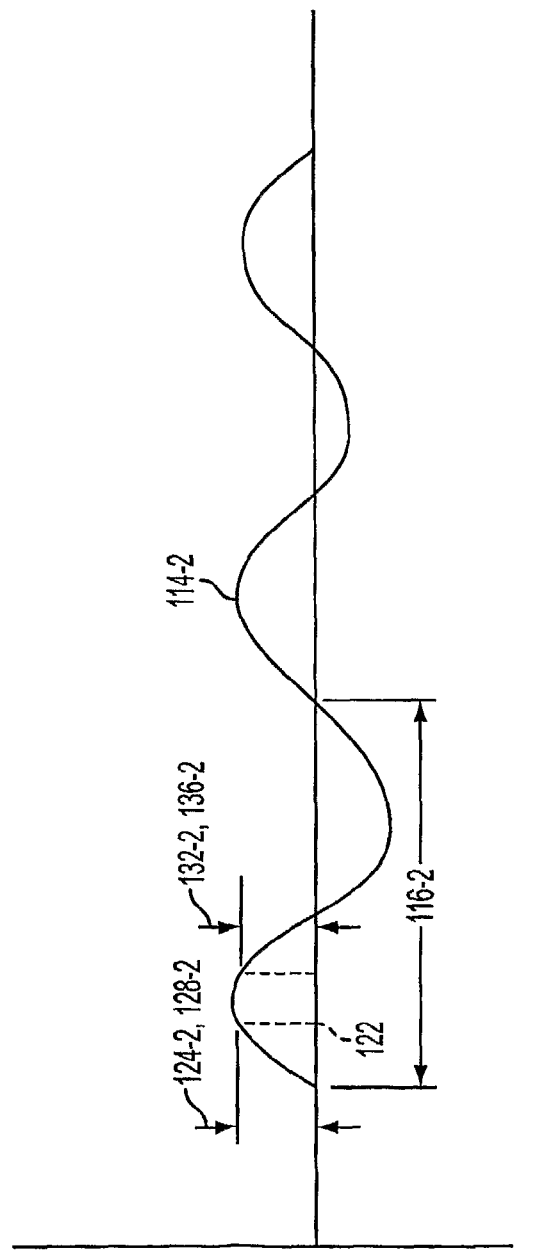

ULTRASOUND IMAGING BEAM-FORMER APPARATUS AND METHOD

CROSS-REFERENCE TO RELATED APPLICATIONS

The present application is a continuation of U.S. application Ser. No. 11/160,915 filed on Jul. 14, 2015, now abandoned which is a continuation of International Application No. PCT/US2004/000887 filed Jan. 14, 2014 which claims priority to U.S. Provisional Application Ser. Nos. 60/440,020 filed on Jan. 14, 2003, 60/439,990 filed on Jan. 14, 2003, and 60/440,262 filed on Jan. 15, 2003 the entire disclosures of which are incorporated herein by reference.

BACKGROUND

1. Field of the Invention

The present invention relates to ultrasonic diagnostic imaging systems and methods. More specifically, the preferred embodiments relate to a device and method for ultrasound imaging beam-forming that may be incorporated in a substantially integrated hand-held ultrasonic diagnostic imaging instrument.

2. Introduction

Medical imaging is a field dominated by high cost systems that may be so complex as to require specialized technicians for operation and the services of experienced medical doctors and nurses for image interpretation. Medical ultrasound, which is considered a low cost modality, utilizes imaging systems costing as much as $250K. These systems may be operated by technicians with two years of training or specialized physicians. This high-tech, high-cost approach works very well for critical diagnostic procedures. However it makes ultrasound impractical for many of the routine tasks for which it would be clinically useful.

A number of companies have attempted to develop low cost, easy to use systems for more routine use. The most notable effort is that by Sonosite. Their system produces very high quality images at a system cost of approximately $20,000. While far less expensive than high-end systems, these systems are still very sophisticated and require a well-trained operator. Furthermore, at this price few new applications may be opened.

Many ultrasonic imaging systems utilize an array transducer that is connected to beamformer circuitry through a cable, and a display that is usually connected directly to or integrated with the beam-former. This approach is attractive because it allows the beamformer electronics to be as large as is needed to produce an economical system. In addition, the display may be of a very high quality.

Some conventional system architectures have been improved upon through reductions in beam-former size. One of the most notable efforts has been undertaken by Advanced Technologies Laboratories and then continued by a spin-off company, Sonosite. U.S. Pat. No. 6,135,961 to Pflugrath et al., entitled "Ultrasonic Signal Processor for a Hand Held Ultrasonic Diagnostic Instrument," hereby incorporated by reference herein in its entirety, describes some of the signal processing employed to produce a highly portable ultrasonic imaging system. The Pflugrath '961 patent makes reference to an earlier patent, U.S. Pat. No. 5,817,024 to Ogle et al., entitled, "Hand Held Ultrasonic Diagnostic instrument with Digital Beamformer," hereby incorporated by reference herein in its entirety. In U.S. Pat. No. 6,203,498 to Bunce et al., entitled "Ultrasonic Imaging Device with Integral Display," hereby incorporated by reference herein in its entirety, however, the transducer, beamformer, and display may be all integrated to produce a very small and convenient imaging system.

Other references of peripheral interest are U.S. Pat. No. 6,669,641 to Poland, et al., entitled "Method of and system for ultrasound imaging," which describes an ultrasonic apparatus and method in which a volumetric region of the body is imaged by biplane images. One biplane image has a fixed planar orientation to the transducer, and the plane of the other biplane image can be varied in relation to the fixed reference image.

U.S. Pat. No. 6,491,634 to Leavitt, et al., entitled "Sub-beam-forming apparatus and method for a portable ultrasound imaging," describes a sub-beam-forming method and apparatus that is applied to a portable, one-dimensional ultrasonic imaging system. The sub-beam-forming circuitry may be included in the probes assembly housing the ultrasonic transducer, thus minimizing the number of signals that are communicated between the probe assembly and the portable processor included in the imaging system.

U.S. Pat. No. 6,380,766 to Savord, entitled "Integrated circuitry for use with transducer elements in an imaging system," describes integrated circuitry for use with an ultrasound transducer of an ultrasound imaging system.

U.S. Pat. No. 6,013,032 to Savord, entitled "Beam-forming methods and apparatus for three-dimensional ultrasound imaging using two-dimensional transducer array," describes an ultrasound imaging system including a two-dimensional array of ultrasound transducer elements that define multiple sub-arrays, a transmitter for transmitting ultrasound energy into a region of interest with transmit elements of the array, a sub-array processor and a phase shift network associated with each of the sub-arrays, a primary beam-former and an image generating circuit.

U.S. Pat. No. 6,126,602 to Savord, et al., entitled "Phased array acoustic systems with intra-group processors," describes an ultrasound imaging apparatus and method that uses a transducer array with a very large number of transducer elements or a transducer array with many more transducer elements than beam-former channels.

U.S. Pat. No. 5,997,479 to Savord, et al., entitled "Phased array acoustic systems with intra-group processors," describes an ultrasound imaging apparatus and method that uses a transducer array with a very large number of transducer elements or a transducer array with many more transducer elements than beam-former channels.

U.S. Pat. No. 6,582,372 to Poland, entitled "Ultrasound system for the production of 3-D images," describes an ultrasound system that utilizes a probe in conjunction with little or no specialized 3-D software/hardware to produce images having depth cues.

U.S. Pat. No. 6,179,780 to Hossack, et al., entitled "Method and apparatus for medical diagnostic ultrasound real-time 3-D transmitting and imaging," describes a medical diagnostic ultrasound real-time 3-D transmitting and imaging system that generates multiple transmit beam sets using a 2-D transducer array.

U.S. Pat. No. 6,641,534 to Smith, et al., entitled "Methods and devices for ultrasound scanning by moving sub-apertures of cylindrical ultrasound transducer arrays in two dimensions," describes methods of scanning using a two dimensional (2-D) ultrasound transducer array.

U.S. Pat. No. 4,949,310 to Smith, et al., entitled "Maltese cross processor: a high speed compound acoustic imaging system," describes an electronic signal processing device which forms a compound image for any pulse-echo ultrasound imaging system using a two-dimensional array transducer.

U.S. Pat. No. 6,276,211 to Smith, entitled "Methods and systems for selective processing of transmit ultrasound beams to display views of selected slices of a volume," describes the selection of a configuration of slices of a volume, such as B slices, I slices, and/or C slices.

Commercial ultrasound systems have been limited to one-dimensional (1-D) or linear transducer arrays until fairly recently. A typical number of transducers in such an array may be 128. Providing separate multiplex and receive circuitry is manageable with this many transducers, albeit with significant use of expensive high-voltage switches. Newer arrays, however, may be likely to be two-dimensional (2-D) or square arrays. The number of transducers in a two-dimensional array may range up to 128×128 or 16,384, and is often in the thousands. Maintaining separate receive, transmit, and multiplex partitioning for the transducers in such an array creates a tremendous burden in terms of cost, space, and complexity. The power consumption and heat dissipation of thousands high-voltage multiplexers is enough to discourage the use of two-dimensional arrays in portable ultrasound imaging systems.

Current beam-forming strategies can be broadly classified into the two approaches depicted in FIG. 5. One approach is to use digital time delays to focus the data, as illustrated in 5(a). Geometric delays are calculated and applied to the digitized data on each channel. In such beam-formers, the data needs to either be sampled at a very high sampling rate or interpolated. Implementation of time delays requires sufficient memory to hold a few hundred samples per channel to implement an adequate delay envelope, constraining system complexity.

In the second approach, systems combine time delays with complex phase rotation, as depicted in 5(b). Coarse focusing is implemented by delaying the digitized data on each channel. Fine focusing is accomplished by phase rotation of data that has undergone complex demodulation at the center frequency. Such systems require circuitry to perform complex demodulation on every channel. Time delay beam-forming requires significant fast memory to implement a reasonable delay envelope.

Conventional approaches to generating I/Q data may also include analog/digital baseband demodulation, or use a Hilbert transform. Using a demodulation based approach to generate I/Q data may necessitate significant extra circuitry on each channel, while use of the Hilbert transform may require a significant amount of memory to hold the raw RF data.

Accordingly, existing ultrasound systems with thousands of separate transmit and receive switches may be too expensive for many applications. While a variety of systems and methods may be known, there remains a need for improved systems and methods.

BRIEF DESCRIPTION OF THE DRAWINGS

The preferred embodiments of the present invention are shown by a way of example, and not limitation, in the accompanying figures, in which:

FIGS. 6A, 6B, and 6C are graphs of signals for use with an embodiment of the invention;

SUMMARY OF THE INVENTION

Figure 1:
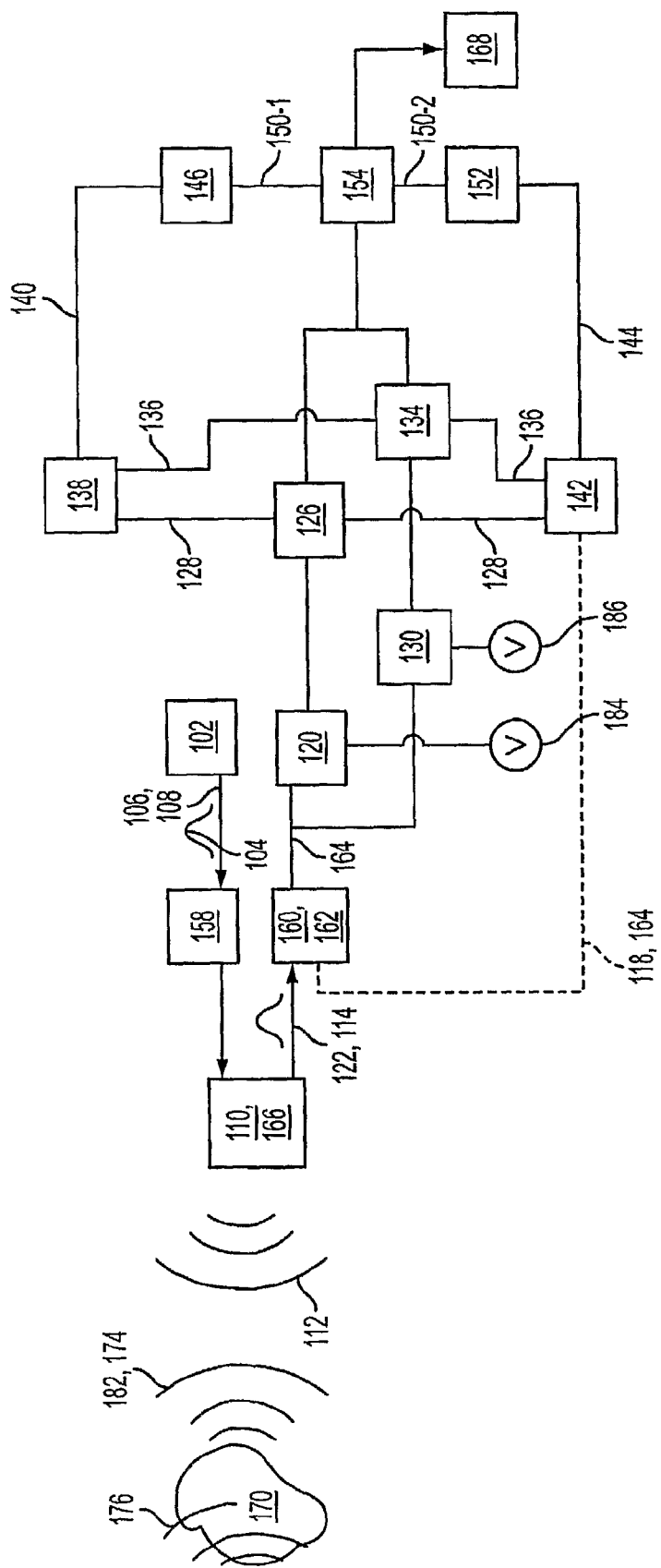
FIG. 1 is a schematic diagram of an ultrasound imaging beam-forming apparatus according to a first embodiment of the invention.

The present invention ultrasound imaging beam-former may be incorporated in an ultrasonic imaging system convenient enough to be a common component of nearly every medical examination and procedure. The present invention ultrasound imaging beam-former provides the potential to have a broad and significant impact in healthcare. The instant document identifies various clinical applications of the present invention ultrasound imaging beam-forming apparatus, but should not be limited thereto, and other applications will become attained as clinicians gain access to the system and method.

The preferred embodiments of the present invention may improve significantly upon existing methods and/or apparatuses. In particular, the present invention comprises an ultrasound imaging beam-former that may be used in a hand held ultrasonic instrument such as one provided in a portable unit which performs B-mode or C-Mode imaging and/or collects three dimensional (3-D) image data.

According to some embodiments, an ultrasound imaging beam-former is provided that includes, in a first aspect of the invention, an ultrasound imaging beam-former apparatus includes a signal generator for producing an outgoing signal, a transducer for converting the outgoing signal to outgoing ultrasound and for converting at least a portion of the outgoing ultrasound that is reflected to an incoming signal, the incoming signal having a period, and a signal receiver for processing the incoming signal, the signal receiver including, an in-phase sample-and-hold connected receivably to the transducer for sampling the incoming signal at an incoming time and outputting an in-phase amplitude of the incoming signal at substantially the incoming time, a quadrature sample-and-hold connected receivably to the transducer for sampling the incoming signal at substantially one-quarter of the period after the incoming time, the quadrature sample-and-hold outputting a quadrature amplitude of the incoming signal at substantially one-quarter of the period after the incoming time, a phase calculator connected receivably to the in-phase sample-and-hold and the quadrature sample-and-hold for receiving the incoming time, the in-phase amplitude, and the quadrature amplitude and outputting a phase, and a phase rotator for applying an illumination to the image point in substantial proportion to the phase.

In a second aspect, a method of beam-forming for ultrasound imaging includes generating an outgoing signal, transducing the outgoing signal to outgoing ultrasound, receiving at least a portion of reflected outgoing ultrasound, transducing the reflected ultrasound to an incoming signal having a period, sampling the incoming signal at an incoming time to produce an in-phase amplitude of the incoming signal, sampling the incoming signal at substantially one-quarter of the period after the incoming time to produce a quadrature amplitude of the incoming signal, calculating a phase at the incoming time based on the in-phase amplitude and the quadrature amplitude, and applying an illumination to the image point in substantial proportion to the phase.

In a third aspect, a system for beam-forming for ultrasound imaging includes means for generating an outgoing signal, means for transducing the outgoing signal to outgoing ultrasound, means for transducing at least a portion of reflected outgoing ultrasound to an incoming signal having a period, means for sampling the incoming signal at an incoming time and outputting an in-phase amplitude of the incoming signal, means for sampling the incoming signal at substantially one-quarter of the period after the incoming time and outputting a quadrature amplitude of the incoming signal, means for calculating a phase at the incoming time, based on the in-phase amplitude and the quadrature amplitude and outputting the phase, means for measuring a difference between the outgoing amplitude and the magnitude, means for applying a first illumination to a image point in substantial proportion to the difference, and means for applying a second illumination to the image point in substantial proportion to the phase.

The above and/or other aspects, features and/or advantages of various embodiments will be further appreciated in view of the following description in conjunction with the accompanying figures. Various embodiments can include and/or exclude different aspects, features and/or advantages where applicable. In addition, various embodiments can combine one or more aspect or feature of other embodiments where applicable. The descriptions of aspects, features and/or advantages of particular embodiments should not be construed as limiting other embodiments or the claims.

DETAILED DESCRIPTION OF THE PREFERRED EMBODIMENTS

The device and method for ultrasound imaging beam-forming may be utilized with various products and services as discussed below, but is not limited thereto. Technicians may attempt to insert needles into a vein based on the surface visibility of the vein coupled with their knowledge of anatomy. While this approach works quite well in thin, healthy individuals, it can prove extremely difficult in patients who may be ill or obese. It may be desirable to have a relatively small, inexpensive, and portable ultrasound imaging system for guiding the insertion of intravenous (IV) devices like needles and catheters into veins, or for drawing blood.

Sleep apnea (obstruction of the air passage in the of the throat) may affect more than eighteen million Americans. Obstructive sleep apnea may be among the most common variants of sleep apnea. Obstructive sleep apnea may represent a significant risk to the patient. It is difficult and expensive to diagnose obstructive sleep apnea. Typical diagnostic methods require an overnight hospital stay in an instrumented laboratory. Many at-risk patients refuse this inconvenient testing regime and thus go undiagnosed. It may be desirable to have a relatively small, inexpensive, and portable ultrasound imaging system to aid in the diagnosis of obstructive sleep apnea in a minimally obtrusive manner.

Manual palpation is an exceedingly common diagnostic procedure. Clinicians use their sense of touch to feel for subcutaneous lumps or even to estimate the size of lymph nodes or other masses. While palpation undoubtedly yields valuable qualitative information, numerous studies have shown it to have extremely poor sensitivity and that quantitative size estimates may be completely unreliable. It may be desirable to have a relatively small, inexpensive, and portable ultrasound imaging system to aid in observing subcutaneous tissues.

It may be desirable to place an image display at a transducer. It may be desirable to have a relatively small, inexpensive, and portable ultrasound imaging system to aid in placing the image display at the transducer.

Ultrasound may be used to search for internal defects in metallic or ceramic parts in a broad variety of industrial applications. Current systems may be cost effective, but may be unwieldy and acquire limited data, making it difficult to ensure that a thorough search has been performed. It may be desirable to have a relatively small, inexpensive, and portable ultrasound imaging system to aid in non-destructive evaluation.

Furthermore, new users may expect ultrasound images to produce representations parallel to the skin's surface, i. e. C-Scan images. It would be desirable for a low cost, system to be capable of producing C-Scan images. It may further be desirable to display data in the intuitive C-scan format to allow clinicians with little or no training in reviewing ultrasound images to make use of the device.

Ultrasound imaging devices may be too expensive for some applications. It may be desirable for an ultrasound imaging device to rely primarily or exclusively on receive side beam-forming to reduce or eliminate transmit-side circuitry, enabling the beam-former to be implemented using large scale integration or as software, and enabling system to be produced at a lower cost.

It may further be desirable for an ultrasound imaging device to rely primarily or exclusively on phase rotation for focusing, enabling the beam-former to be implemented using large scale integration or as software, and enabling system to be produced at a lower cost.

Ultrasound imaging devices may be insufficiently portable for some applications. It may be desirable for an ultrasonic imaging device to be of a small size to make it easy to carry the device in a pocket or on a belt attachment. This may make the device as convenient as a stethoscope and will thus open new applications. It may be desirable for an ultrasound imaging device to rely primarily or exclusively on receive side beam-forming to reduce or eliminate transmit-side circuitry, enabling the beam-former to be implemented using large scale integration or as software, and enabling the system to be made portable. It may further be desirable for an ultrasound imaging device to rely primarily or exclusively on phase rotation for focusing to reduce or eliminate transmit-side circuitry, enabling the beam-former to be implemented using large scale integration or as software, and enabling the system to be made portable.

Since it would be desirable for a beam-former to be simple, small, and low cost, it would be further desirable for the size and speed requirements of digital memory in such a beam-former to be minimized. It would be further desirable for focusing to be performed solely by phase rotation of I/Q data, thus eliminating the need for some circuitry, and allowing some of the remaining circuitry to be implemented as an integrated circuit. This may also allow the use of slower memory and reduce the computational complexity of the beam-former.

It would be further desirable for I/Q data to be generated by sampling an RF signal directly converting the RF signal to a pair or a time series of pairs of in phase and quadrature samples. In one embodiment, an analytic signal (I/Q data) is generated by sampling the received RF signal directly, in a manner analogous to the Hilbert transform. In one embodiment, focusing is implemented via phase rotation of this I/Q data.

Figure 6A:
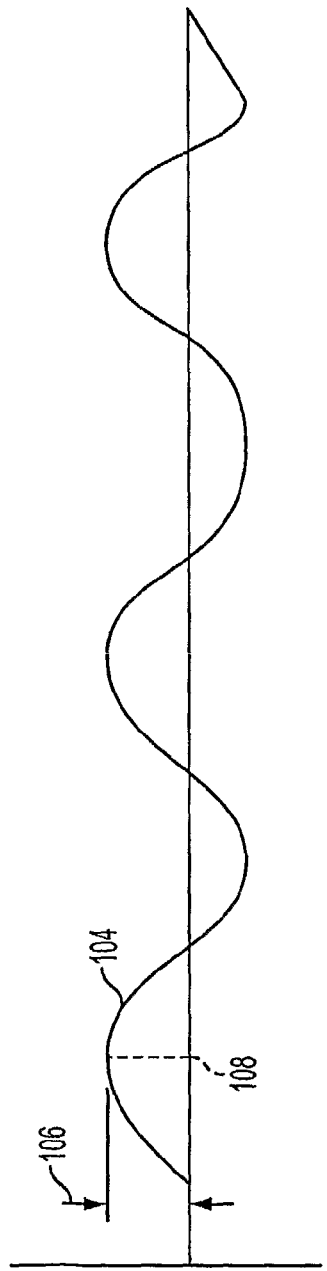

In FIG. 1 is shown an ultrasound imaging beam-former apparatus 100 according to a first embodiment of the invention. Ultrasound imaging beam-former apparatus 100 may include a signal generator 102 for producing an outgoing signal 104 having an outgoing amplitude 106 at an outgoing time 108, as shown in FIG. 6A. In several embodiments, outgoing signal 104 may be an electrical signal, an electromagnetic signal, or an optical signal.

If outgoing signal 104 is an optical signal, cross-talk between the circuits of ultrasound imaging beam-former apparatus 100 may be reduced or eliminated, since optical signals do not, in general, interfere with one another. This may allow ultrasound imaging beam-former apparatus 100 to be made smaller than an equivalent electronic device by increasing the density of the circuits. In one case, outgoing signal 104 may be processed as an optical signal and converted to an electrical signal to drive a transducer. An integrated circuit comprising ultrasound imaging beam-forming apparatus 100 may be implemented out of gallium-arsenide (GaAs) so that the both the optical circuits and the electrical circuits can be implemented on the same device. In another case, a transducer utilizing sono-luminescence to convert light directly into sound may be used, dispensing entirely with any need for an electrical-optical interface.

In several embodiments, signal generator 102 may be a storage device, such as a read-only memory (ROM), an oscillator such as a crystal oscillator, a resonant circuit such as a resistor-inductor-capacitor (RLC) or tank circuit, a resonant cavity such as a ruby laser or a laser diode or a tapped delay line.

In the event that signal generator 102 is a storage device, outgoing signal 104 may have been stored previously, to be read out when needed. In this embodiment, several versions of outgoing signal 104 may be stored for use with various objects 170 to be imaged. Ultrasound imaging beam-forming apparatus 100 may thus be set to produce a signal appropriate for a particular object 170 to be imaged by choosing one of the stored versions of outgoing signal 104.

In the event that signal generator 102 is an oscillator, outgoing signal 104 may be a sinusoid of varying frequencies. In this case, outgoing signal 104 may be generated at an arbitrarily high clock speed and still be forced through filters of arbitrarily small bandwidth. This may be advantageous, for example, if a wide band signal is inconvenient. A resonant circuit or a resonant cavity may work in a similar manner. Furthermore, an oscillator may be used to produce a range of frequencies, from which a frequency that generates an optimum response may be selected.

In the event that signal generator 102 is tapped delay line, outgoing signal 104 could be generated in a manner similar to a spreading code in a code division multiple access (CDMA) format cell phone system. In this case outgoing signal 104 would not need to be a pure sinusoid, but may be a code with a fixed repetition length, such as a Walsh or a Gold code. This may, for example, allow an autocorrelation length of outgoing signal 104 to be adjusted to enhance or suppress coded excitation of an incoming signal.

If signal generator 102 is a tapped delay line it may be followed by an equalizer to bias or pre-emphasize a range of frequencies in outgoing signal 104. In one embodiment, the equalizer may be an adaptive equalizer that operates on an incoming signal analogous to the sound reflected by the imaged object 170. In this case, the incoming signal could be measured and the result applied to the adaptive equalizer to compensate for frequency attenuation of the sound by amplifying one or more frequencies of the incoming signal or outgoing signal 104 as necessary. This may be useful if, for example, object 170 attenuates or absorbs sound to the point that no return signal is available for imaging. In one embodiment, the adaptive equalizer could be placed in parallel with signal generator 102 and in series with the incoming signal.

In one embodiment, an equalizer could be placed in series with signal generator 102. In this case the equalizer could emphasize a particular frequency or frequencies in outgoing signal 104. The equalizer may, for example, place a bias or pre-emphasis toward lower frequencies on outgoing signal 104. This embodiment may be appropriate if, for example, object 170 to be imaged is expected to have features that attenuate lower frequencies significantly more than higher frequencies to the extent that imaging may be difficult. The converse may be true as well, in that the equalizer may have a bias or pre-emphasis toward higher frequencies.

In one embodiment, outgoing signal 104 may be amplified. In one embodiment, signal generator 102 may include a generator amplifier 158 for amplifying outgoing signal 104. Generator amplifier 158 may pre-emphasize certain frequencies of outgoing signal 104 to suit the attenuation characteristics of object 170 to be imaged as well. Signal generator 102 may also include an oscillator to produce an appropriate modulation frequency, such as a radio frequency (RF) signal, with which to modulate outgoing signal 104.

A transducer 110 may convert outgoing signal 104 to outgoing ultrasound 112. In several embodiments, transducer 110 may be a piezoelectric element, a voice coil, a crystal oscillator or a Hall effect transducer 110. In one embodiment, reversals of outgoing signal 104 produce vibration of a surface of transducer 110 at substantially the frequency of outgoing signal 104. In another embodiment, reversals of outgoing signal 104 produce vibrations of a surface of transducer 110 at frequencies that are significantly higher or lower than the frequency of outgoing signal 104, such as harmonics of outgoing signal 104. This vibration may, in turn, produce successive compressions and rarefactions of an atmosphere surrounding the surface of transducer 110, also at substantially the frequency of outgoing signal 104. If the frequency of outgoing signal 104 is substantially higher than a frequency at which sound may be heard, the successive compressions and rarefactions of the atmosphere may be termed ultrasound.

In one embodiment, transducer 110 may include a plurality of transducers 110. In one embodiment, plurality of transducers 110 may be arranged in an array 166. In several embodiments, array 166 may be a linear array, a phased array, a curvilinear array, an unequally sampled 2-D array, a 1.5-D array, an equally sampled 2D array, a sparse 2D array, or a fully sampled 2D array.

Figure 6B:
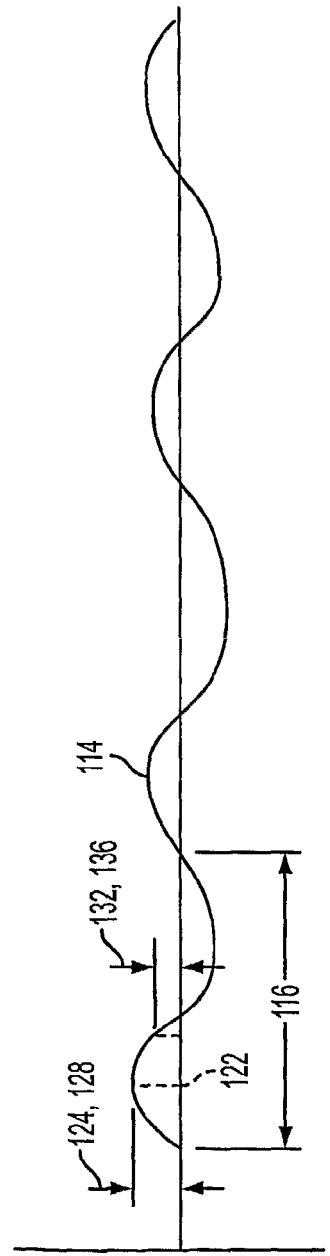

If outgoing ultrasound 112 is reflected by object 170, some of outgoing ultrasound 112 may return to ultrasound imaging system 100 as reflected ultrasound 182. Reflected ultrasound 182 may be converted to an incoming signal 114 having a period 116, as shown in FIG. 6B. In several embodiments, incoming signal 114 may be an electro-magnetic signal, an electrical signal or an optical signal. In several embodiments, incoming signal 114 may be amplified, pre-amplified, or stored.

In one embodiment, outgoing ultrasound 112 may be delayed or attenuated partially by object 170. A first portion 174 of outgoing ultrasound 112, for example, may be reflected immediately upon encountering a nearer surface 178 of object 170 while a second portion 176 of outgoing ultrasound 112 is not reflected until it encounters a further surface 180 of object 170. A round trip of second portion 176 will thus be longer than a round trip of first portion 174, resulting in a delay of second portion 176 relative to first portion 174, as well as delays of both first and second portions 174, 176 relative to outgoing ultrasound 112. Furthermore, second portion 176 may be damped or attenuated by a material of object 170. The delays may be measured for disparate points of object 170, producing an image 168 of object 170.

Apparatus 100 may include a signal receiver 118 for processing incoming signal 114. In one embodiment, signal receiver 118 may be implemented as a digital signal processor 164. In one embodiment, signal receiver 118 may be implemented as an integrated circuit.

Ultrasonic transducers associated with ultrasound imaging systems may be driven from a single terminal with the second terminal grounded. A transducer may be used to transmit ultrasound signals as well as receive reflected ultrasound. A signal received at a transducer may typically be several orders of magnitude smaller than the signal that was transmitted due to, inter alia, signal attenuation by the target tissue. Some of the signal may be lost due to transducer inefficiencies as well. It may be thus necessary to couple the transducer to a high-voltage transmit signal while the ultrasound is being transmitted, and then to a sensitive low-noise pre-amplifier while the reflected ultrasound is being received.

A switch that couples the transducer to the transmit and receive signals must be capable of withstanding high peak transmit voltages (typically 50-200 volts) while isolating the pre-amplifier input from those voltage levels, since they would otherwise destroy the pre-amplifier. If a receiver for the signals from the transducers is implemented as a high-density, low-voltage integrated circuit (IC), the switches themselves may need to be implemented off-chip in a separate package from materials and devices that can withstand the high voltage transmit pulses.

Figure 2:
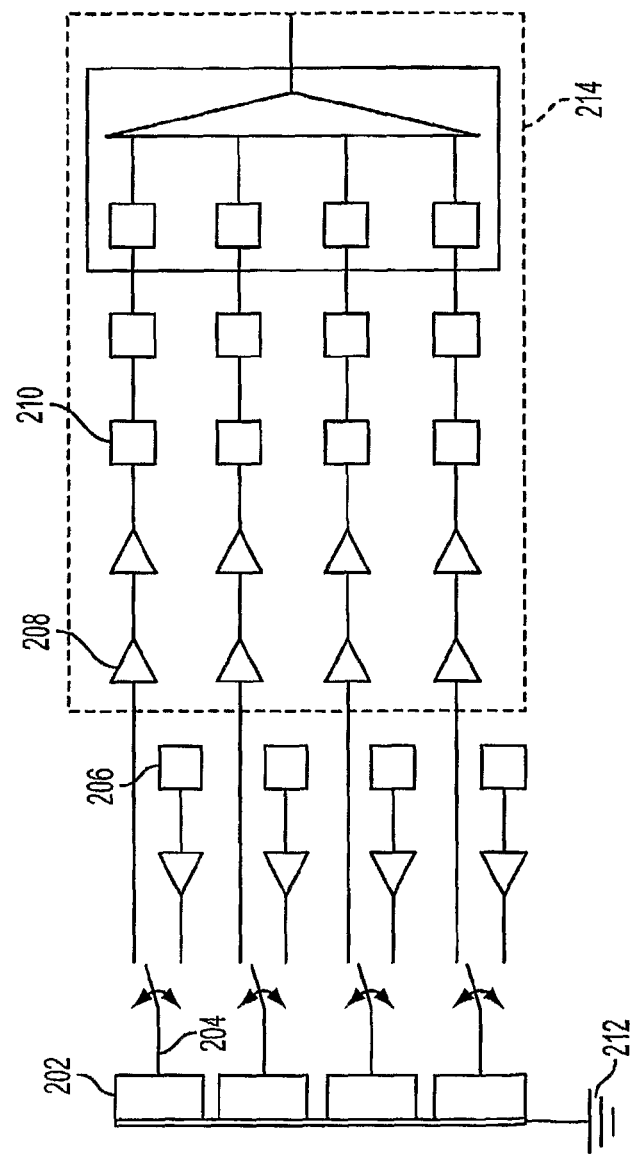
FIG. 2 is a schematic diagram of a protection circuit for use with an embodiment of the invention.

In one embodiment, ultrasound imaging system 100 may include a protection circuit 172 to allow both transmit and receive operations, as shown in FIG. 2. A piezoelectric transducer array 202, shown on the left, acts as an interface to a signal processor by converting electrical signals to acoustic pulses and vice versa. Images may be formed by transmitting a series of acoustic pulses from the transducer array 202 and displaying signals representative of the magnitude of the echoes received from these pulses. A beam-former 214 applies delays to the electrical signals to steer and focus the acoustic pulses and echoes.

Image formation begins when a state of a transmit/receive switch (TX/RX switch) 204 is altered to connect the transducer elements 202 to individual transmit circuits. Next, transmit generators 206 output time varying waveforms with delay and amplitude variations selected to produce a desired acoustic beam. Voltages of up to 200 Volts may be applied to the transducer elements 202. Once transmission is complete, the state of the TX/RX switch 204 is altered again to connect the transducer elements 202 to individual receive circuitry associated with each element.

Signals representative of incoming echoes may be amplified by pre-amplifiers 208 and time gain control (TGC) 210 circuits to compensate for signal losses due to diffraction and attenuation. Note that the transducer array 202 shown in FIG. 2 has one common electrode 212, and the non-common electrodes may be multiplexed between high-voltage transmit and low-voltage receive signals. This conventional TX/RX switch 204 is the source of considerable expense and bulk in typical ultrasound systems.

Figure 3:
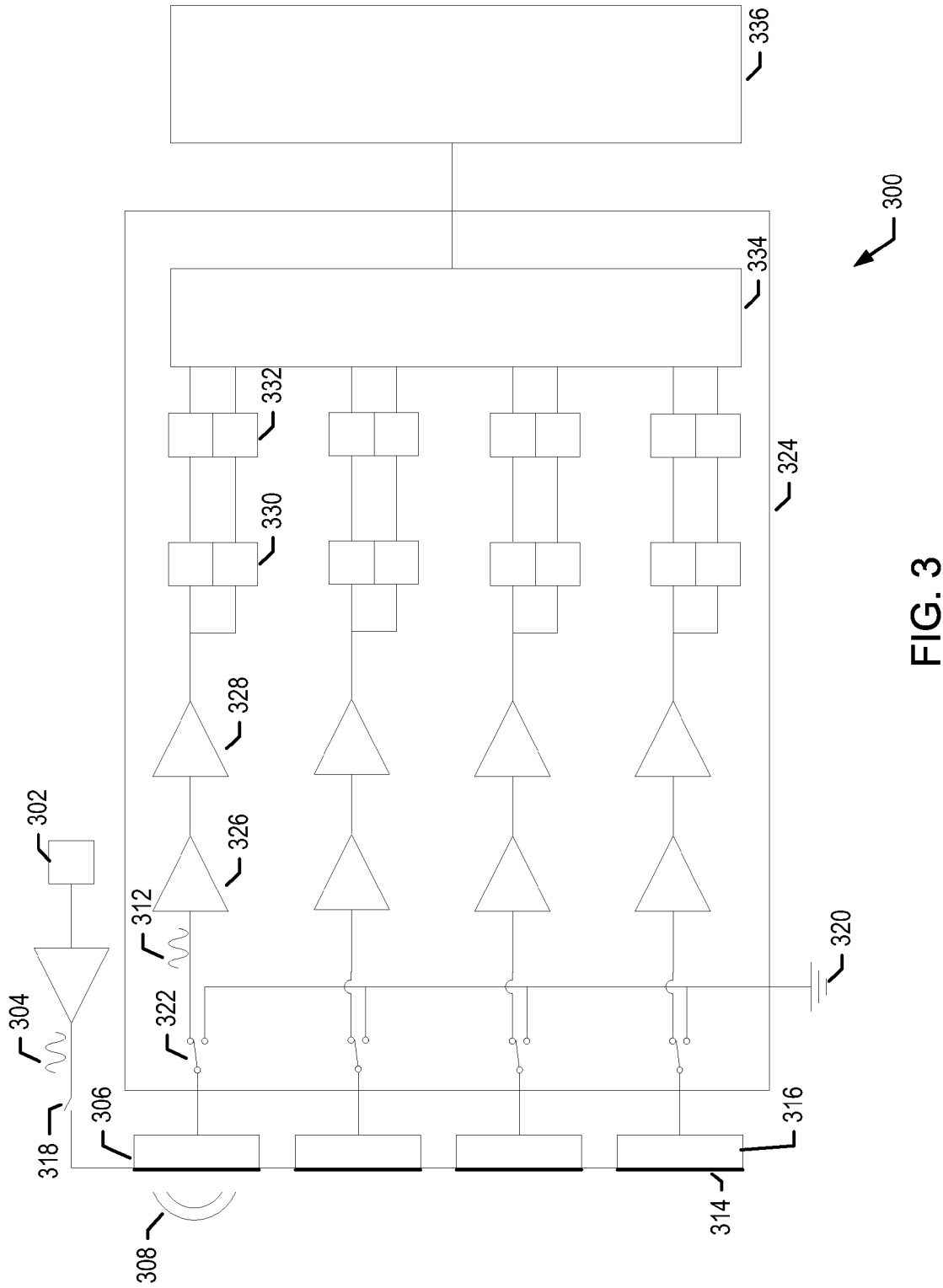
FIG. 3 is a schematic diagram of a protection circuit for use with an embodiment of the invention.

In FIG. 3 is shown an alternative ultrasound imaging beam-forming apparatus 300 with a protection circuit for use with an embodiment of the invention. Ultrasound imaging beam-forming apparatus 300 may include a signal generator 302 for producing an outgoing signal 304.

Ultrasound imaging beam-forming apparatus 300 may also include a transducer 306 for converting outgoing signal 304 to outgoing ultrasound 308 at a frequency of outgoing signal 304. In one embodiment, transducer 306 may have a transmit side 314 forming an interface with outgoing signal 304.

In one embodiment, transmit side 314 may be connected operably to a transmit switch 318. In several embodiments, transmit switch 318 may be an electronic switch, an optical switch, a micro-mechanical switch, a transistor, a field-effect transistor (FET), a bi-polar transistor, a metal-oxide-semiconductor (MOS) transistor, a complementary metal-oxide-semiconductor (CMOS) transistor, or a metal-oxide-semiconductor field-effect transistor (MOSFET). Transmit switch 318 may be connected switchably to signal generator 302 and a ground 320.

In one embodiment, transducer 306 may convert at least a portion of reflected ultrasound 310 to an incoming signal 312. In several embodiments, incoming signal 312 may be an electro-magnetic signal, an electrical signal, or an optical signal. In one embodiment, transducer 306 may have a receive side 316 forming an interface with incoming signal 312.

In one embodiment, receive side 316 may be connected operably to a receive switch 322. In several embodiments, receive switch 322 may be an electronic switch, an optical switch, a micro-mechanical switch, a transistor, a field-effect transistor, a bi-polar transistor, a MOS transistor, a CMOS transistor, or a MOSFET transistor. Receive switch 322 may be connected switchably to a signal receiver 324 and ground 320.

In one embodiment, transmit switch 318 may connect transmit side 314 to signal generator 302 for a first predetermined period of time while signal generator 302 generates outgoing signal 304. In this embodiment, receive switch 322 may connect receive side 316 to signal receiver 324 for a second predetermined period of time while signal receiver 324 receives incoming signal 312. Transmit switch 318 may connect transmit side 314 to ground 320 during substantially second predetermined period of time while signal receiver 324 receives incoming signal 312, and receive switch 322 may connect receive side 316 to ground 320 during substantially first predetermined period of time while signal generator 302 generates outgoing signal 304. In one embodiment, transmit side 314 and receive side 316 are on separate transducers 306.

Figure 8:
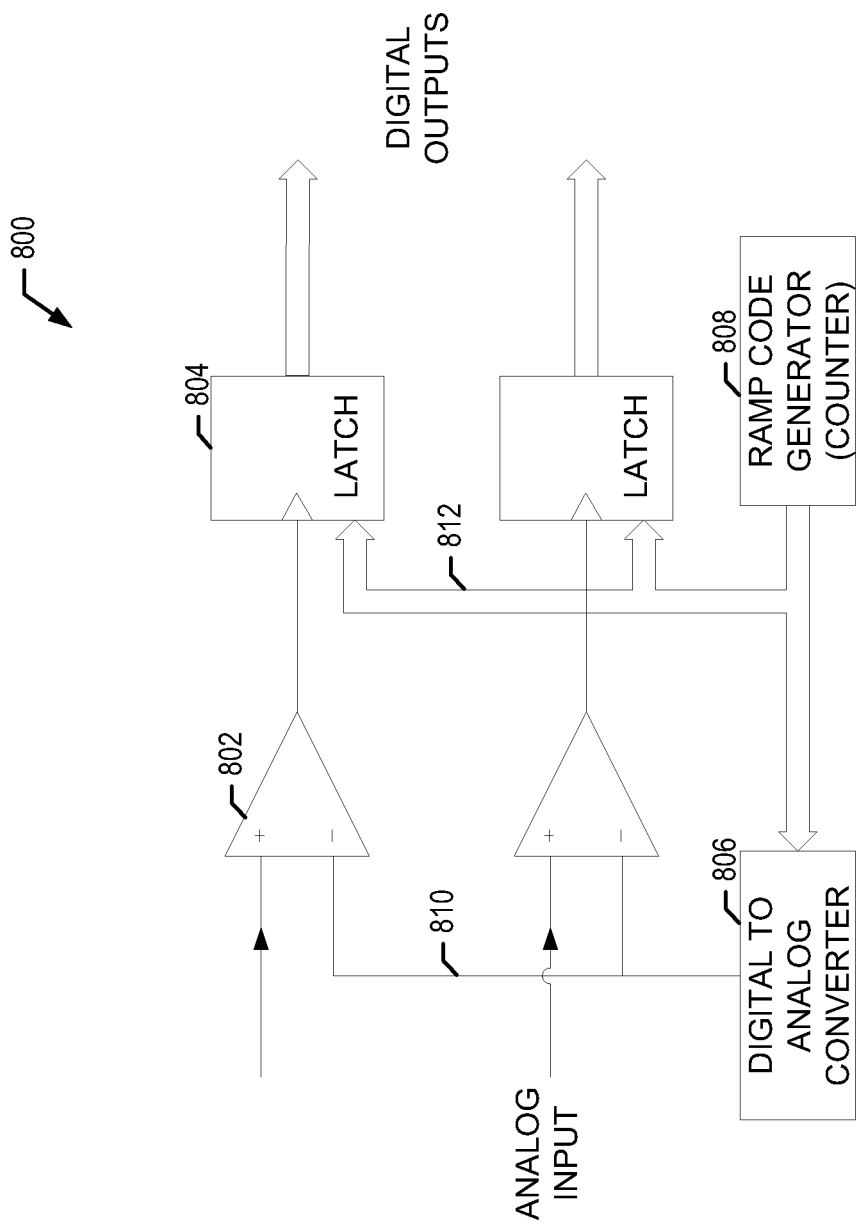

In one embodiment, the incoming signal 312 is amplified by a preamplifier 326. After amplification Time Gain Control (TGC) 328 further amplifies the signal to compensate for signal losses associated with diffraction and attenuation. Next the signal enters two sample and holds (S/H) circuits 330 which sample data over a few ns and hold their outputs for as long as one ms. Sampling is performed once per transmit event, with the two S/H on each channel offset by ¼ period at the ultrasound center frequency to provide an approximate measure of the in-phase and quadrature components (I and Q signals) of the incoming echo. After sampling, the I and Q signals are digitized at the Pulse Repetition Frequency (PRF) with analog-to-digital converters 332. Since only one sampling operation is performed per transmit event, the Analog to Digital (A/D) design is much simpler and the resultant data rate is significantly lower than for a comparable conventional system. Digitized data will be temporarily stored in registers on the custom IC 334 before being read out by a programmable DSP 336. The programmable DSP 336 performs beamforming via software. In one embodiment, simplest beamforming strategy would be to apply complex weightings to each element signal and then sum these to focus and calculate an individual image pixel. This low digitizing rate requirement allows implementation of an array based A/D structure as illustrated in FIG. 8. With this approach a comparator 802 and latch 804 comprise all the hardware required for each channel, yielding an extremely compact and low-power solution appropriate for a high channel count integrated solution. A single DAC 806 and counter 808 are used to provide an analog ramp 810 to the comparators and a synchronized count sequence 812 is provided to the latches. When the DAC output matches the analog input from a sampler, the latch is clocked, preserving the current digital counter output in the channel latch.

In one embodiment, signal receiver 118 may include a receiver amplifier 160 for amplifying incoming signal 114. In one embodiment, signal receiver 118 may include a receiver pre-amplifier 162 for amplifying incoming signal 114. In one embodiment, signal receiver 118 may include a band-pass filter 164 for filtering incoming signal 114.

In one embodiment, signal receiver 118 may include an in-phase sample-and-hold 120 connected receivably to transducer 110 for sampling incoming signal 114 at an incoming time 122 and outputting an in-phase amplitude 124 of incoming signal 114 at substantially incoming time 122. In one embodiment, signal receiver 118 may include an in-phase analog-to-digital converter 126 connected receivably to in-phase sample-and-hold 120 for assigning an in-phase digital value 128 to in-phase amplitude 124 and outputting in-phase digital value 128.

In one embodiment, signal receiver 118 may include a quadrature sample-and-hold 130 connected receivably to transducer 110 for sampling incoming signal 114 at substantially one-quarter of period 116 after incoming time 122, quadrature sample-and-hold 130 outputting a quadrature amplitude 132 of incoming signal 114 at substantially one-quarter of period 116 after incoming time 122. One-quarter of period 116 is merely exemplary. Incoming signal 114 may be sampled at any appropriate interval or fraction of period 116. In one embodiment, signal receiver 118 may include a quadrature analog-to-digital converter 134 connected receivably to quadrature sample-and-hold 130 for assigning a quadrature digital value 136 to quadrature amplitude 132 and outputting quadrature digital value 136.

In one embodiment, signal receiver 118 may include a magnitude calculator 138 connected receivably to in-phase analog-to-digital converter 126 and quadrature analog-to-digital converter 134 for receiving incoming time 122, in-phase digital value 128, and quadrature digital value 136 and outputting a magnitude 140. In one embodiment, signal receiver 118 may include a phase calculator 142 connected receivably to in-phase analog-to-digital converter 126 and quadrature analog-to-digital converter 134 for receiving incoming time 122, in-phase digital value 128, and quadrature digital value 136 and outputting a phase 144.

In one embodiment, incoming signal 114 may be band-pass filtered by band-pass filter 164 and diverted to in-phase sample-and-hold 120 and quadrature sample-and-hold 130. An in-phase clock signal 184 driving in-phase sample-and-hold 120 may be of the same frequency as a quadrature clock signal 186 driving quadrature sample-and-hold 130. Quadrature clock signal 186 may, however, be offset by a quarter of period 116 with respect to in-phase clock signal 184 at an assumed center frequency of incoming signal 114. An output of in-phase sample-and-hold 120 may be digitized by in-phase analog-to-digital converter 126 while an output of quadrature sample-and-hold 130 is digitized in quadrature analog-to-digital converter 134, forming I and Q channel data.

Reflected ultrasound 182 may be considered to be real part of an amplitude and phase modulated complex exponential signal, or analytic signal. The modulating signal may be expressed mathematically as:

$$A(t)e^{j\phi(t)}$$

with instantaneous amplitude A(t) and phase φ(t). This is superimposed on a carrier signal $e^{-j\omega_0 t}$, where $\omega_0 = 2\pi f_0$ and $f_0$ is the frequency of the signal. Therefore the analytic signal S(t) can be written as, $$S(t) = A(t)e^{-j(\omega_0 t - \phi(t))} \qquad (1)$$
$$= A(t)\cos(\omega_0 t - \phi(t)) - jA(t)\sin(\omega_0 t - \phi(t))$$

Only the real part of S (t), which is equivalent to reflected ultrasound 182, is able to be acquired experimentally.

$$I(t) = Re\{S(t)\} = A(t)\cos(\omega_0 t - \phi(t)) \qquad (2)$$

The output of in-phase analog-to-digital converter 126 is the signal in equation 2 after sampling, or $$\hat{I}(nT) = I(nT) = A(nT)\cos(\omega_0 nT - \phi(nT)), n = 0,1,2,3\ldots \qquad (3)$$

where T is the sample interval. However, we also require the imaginary component of S (t), shown below in equation 4, to perform beam-forming.

$$Q(t) = Im\{S(t)\} = -A(t)\sin(\omega_0 t - \phi(t)) \qquad (4)$$

Figure 7:
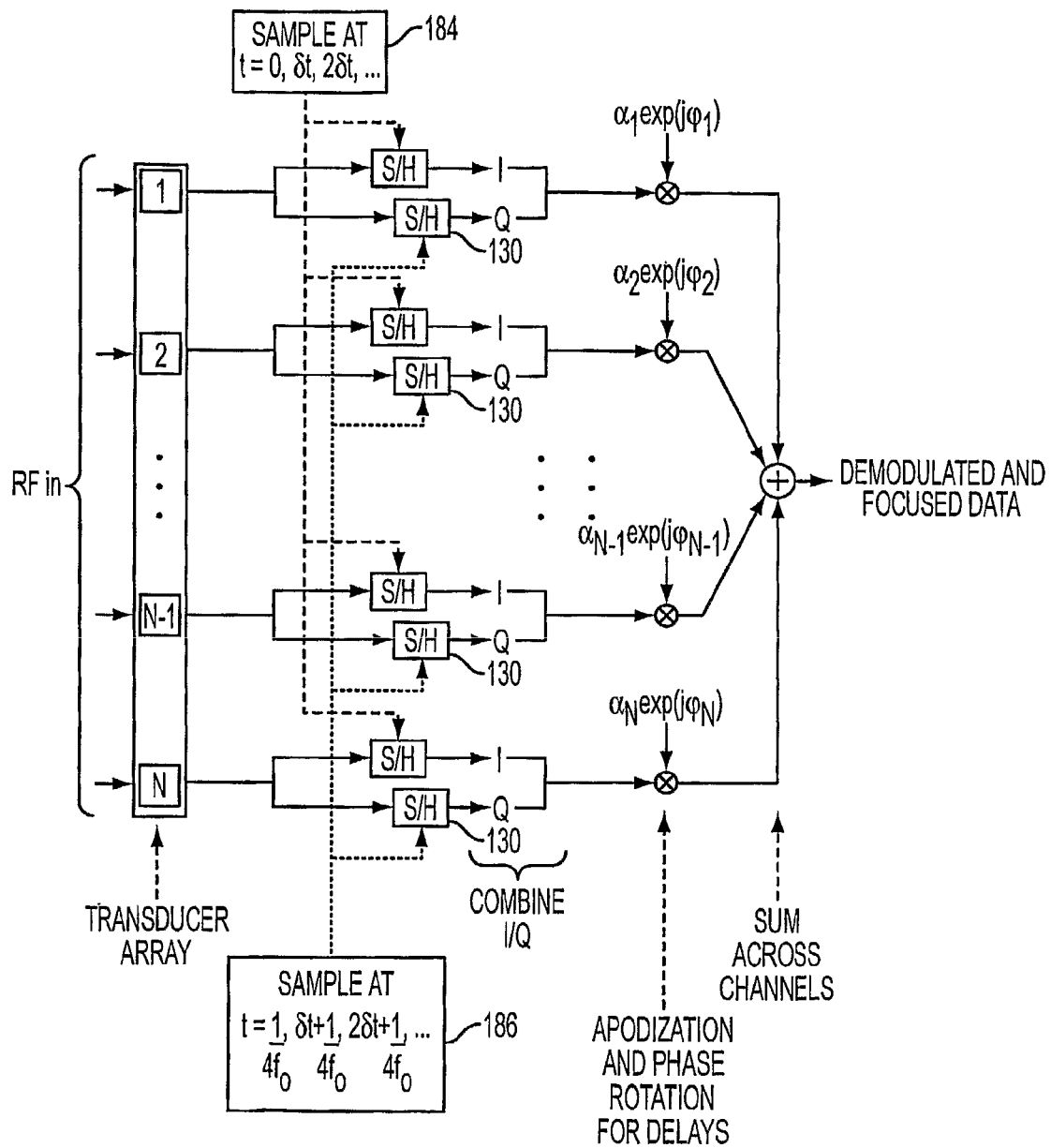
FIG. 7 is a schematic diagram of a signal receiver for use with an embodiment of the invention; and, FIG. 8 is an embodiment of an analog-to-digital converter.

Quadrature clock signal 186 has a time lag of a quarter period at the assumed center frequency relative to the in-phase clock signal 184, as shown 1 schematically in FIG. 7. Therefore the relative time lag is:

$$\frac{1}{4f_0}, \text{ or } \frac{\pi}{2\omega_0}.$$

The output of quadrature sample-and-hold 130 is, $$\hat{Q}(nT) = I\left\{nT + \frac{\pi}{2\omega_0}\right\} \qquad (5)$$
$$= A\left(nT + \frac{\pi}{2\omega_0}\right)\cos\left(\omega_0\left(nT + \frac{\pi}{2\omega_0}\right) - \phi\left(nT + \frac{\pi}{2\omega_0}\right)\right)$$

We assume that the modulating signal $A(t)e^{j\phi(t)}$ varies slowly with time and approximate, $$A\left(nT + \frac{\pi}{2\omega_0}\right) \approx A(nT) \qquad (6)$$

and $$\phi\left(nT + \frac{\pi}{2\omega_0}\right) \approx \phi(nT) \qquad (7)$$

Equation 5 can now be rewritten as follows.

$$\hat{Q}(nT) \approx A(nT)\cos\left(\omega_0\left(nT + \frac{\pi}{2\omega_0}\right)\right), n = 0, 1, 2, 3, \ldots \qquad (8)$$
$$\approx -A(nT)\sin(\omega_0 nT - \phi(nT))$$
$$\approx Q(nT)$$

We therefore approximate the imaginary component of S(t), or Q(t) in equation 4, by estimating it to be the output of quadrature sample-and-hold 130.

Geometric time delays may be calculated and converted to phase delays at the assumed center frequency. Complex weights that implement apodization and focus with the calculated phase delays may be applied to the I/Q data. The I/Q data, also known as a complex echo signal, is multiplied by complex weightings, the result is then summed across the array elements to focus at a specific point. The phase of the complex weightings is used to compensate for the path length difference between a transducer element and a focal point. The magnitude of the complex weightings is selected to maintain a reasonable balance between mainlobe resolution and sidelobe levels in the system response. In one embodiment, signal receiver 118 may include an apodizer 146 for applying a difference 148 between outgoing amplitude 106 and magnitude 140 and applying a first illumination 150-1 to an image points 154 in substantial proportion to difference 148. In one embodiment, signal receiver 118 may include a phase rotator 152 for applying a second illumination 150-2 to image point 154 in substantial proportion to phase 144.

Figure 4:
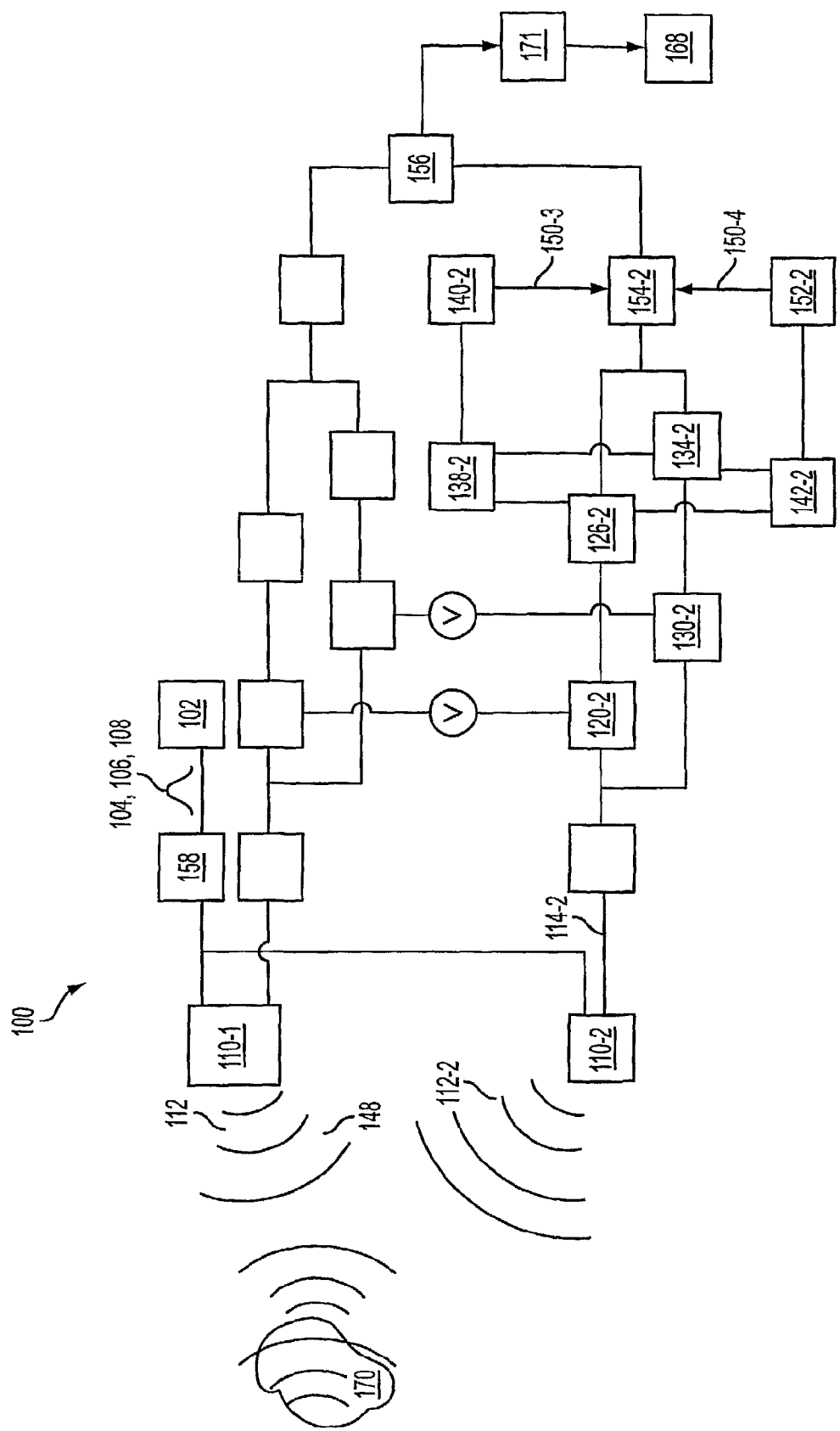
FIG. 4 is a schematic diagram of an ultrasound imaging beam-forming apparatus according to a second embodiment of the invention.
Figure 5A:
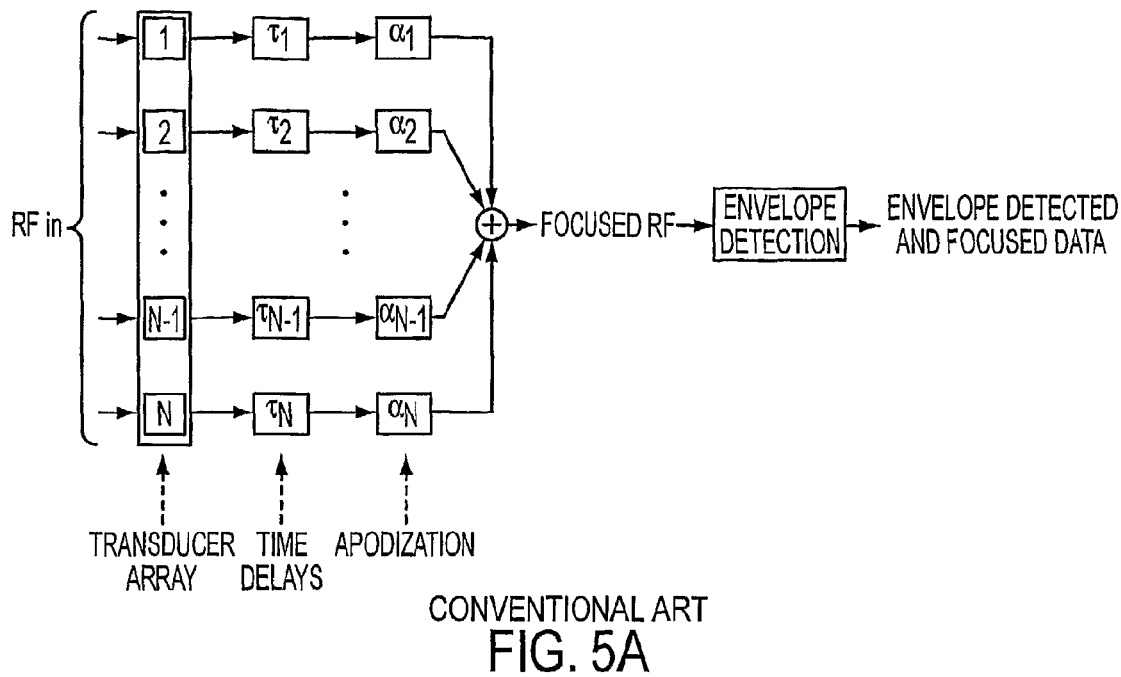
FIGS. 5A and 5B are schematic diagrams of conventional ultrasound imaging beam-forming apparatuses.
Figure 5B:
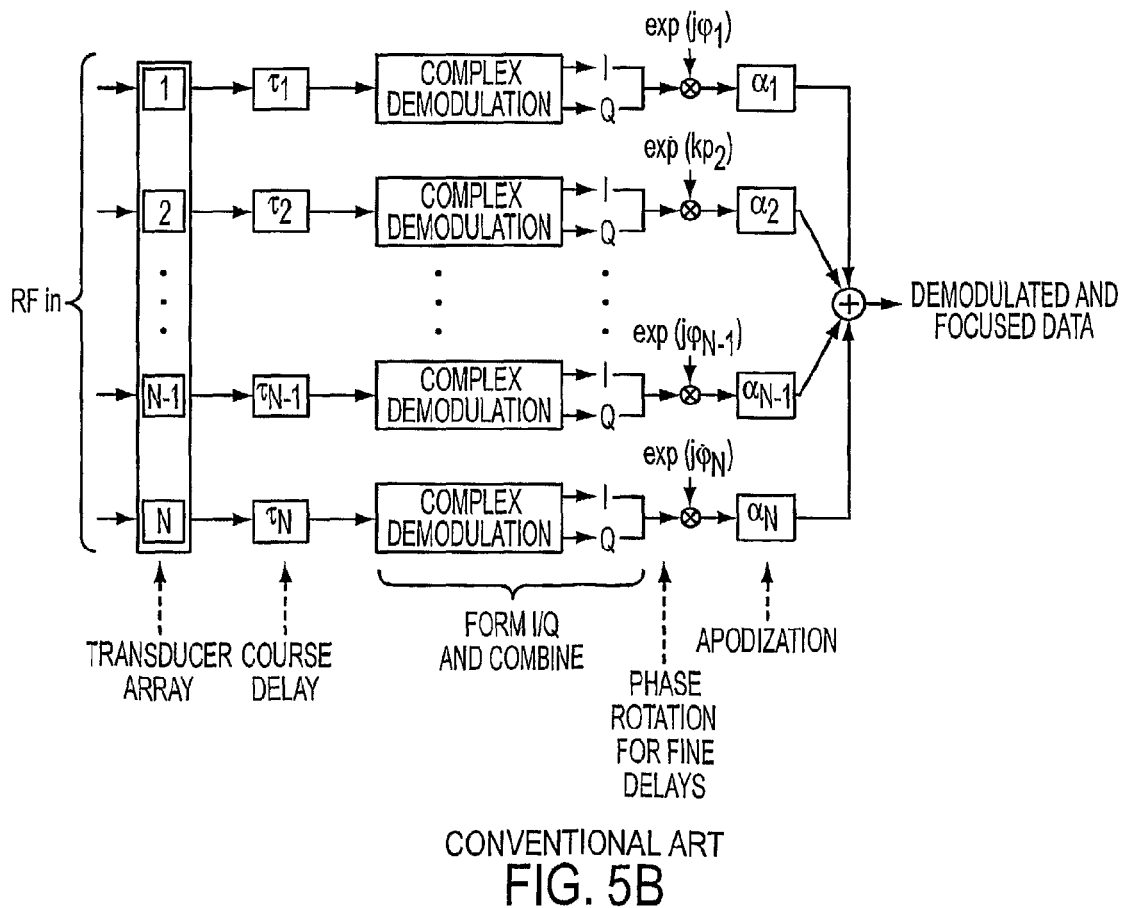

In a second embodiment of the invention, shown in FIG. 4, apparatus 100 may include a second transducer 110-2 for converting outgoing signal 104 to second outgoing ultrasound 112-2. Some of second outgoing ultrasound 112-2 may return to second transducer 110-2 if it is reflected by object 170 as well. Second transducer 110-2 may convert at least a portion of outgoing ultrasound 112 and second outgoing ultrasound 112-2 to a second incoming signal 114-2 having a second period 116-2, as shown in FIG. 6C.

In one embodiment, signal receiver 118 may include a second in-phase sample-and-hold 120-2 connected receivably to second transducer 110-2 for sampling second incoming signal 114-2 at incoming time 122 and outputting a second in-phase amplitude 124-2 of second incoming signal 114-2 at substantially incoming time 122. In one embodiment, signal receiver 118 may include a second in-phase analog-to-digital converter 126-2 connected receivably to second in-phase sample-and-hold 120-2 for assigning a second in-phase digital value 128-2 to second in-phase amplitude 124-2 and outputting second in-phase digital value 128-2.

In one embodiment, signal receiver 118 may include a second quadrature sample-and-hold 130-2 connected receivably to second transducer 110-2 for sampling second incoming signal 114-2 at substantially one-quarter of second period 116-2 after incoming time 122, second quadrature sample-and-hold 130-2 outputting a second quadrature amplitude 132-2 of second incoming signal 114-2 at substantially one-quarter of second period 116-2 after incoming time 122. In one embodiment, signal receiver 118 may include a second quadrature analog-to-digital converter 134-2 connected receivably to second quadrature sample-and-hold 130-2 for assigning a second quadrature digital value 136-2 to second quadrature amplitude 132-2 and outputting second quadrature digital value 136-2. In one embodiment, signal receiver 118 may include a second magnitude calculator 138-2 connected receivably to second in-phase analog-to-digital converter 126-2 and second quadrature analog-to-digital converter 134-2 for receiving incoming time 122, second in-phase digital value 128-2, and second quadrature digital value 136-2 and outputting a second magnitude 140-2. In one embodiment, signal receiver 118 may include a second phase calculator 142-2 connected receivably to second in-phase analog-to-digital converter 126-2 and second quadrature analog-to-digital converter 134-2 for receiving incoming time 122, second in-phase digital value 128-2, and second quadrature digital value 136-2 and outputting a second phase 144-2.

In one embodiment, signal receiver 118 may include a second apodizer 146-2 for applying a second difference 148-2 between outgoing amplitude 106 and second magnitude 140-2 and applying a third illumination 150-3 to an image point 154 in substantial proportion to second difference 148-2. In one embodiment, signal receiver 118 may include a second phase rotator 152-2 for applying a fourth illumination 150-4 to image point 154 in substantial proportion to second phase 144-2. In one embodiment, signal receiver 118 may include a summer 156 for combining difference 148, second difference 148-2, phase 144, and second phase 144-2 before first, second, third, and fourth illuminations 150-1-150-4 are applied to image point 154.

In a third embodiment, a method of beam-forming for ultrasound imaging may include the steps of generating an outgoing signal 104 having an outgoing amplitude 106 at an outgoing time 108, transducing outgoing signal 104 to outgoing ultrasound 112, receiving at least a portion of reflected outgoing ultrasound 112, transducing reflected ultrasound to an incoming signal 114 having a period 116, sampling incoming signal 114 at an incoming time 122 to produce an in-phase amplitude 124 of incoming signal 114, assigning an in-phase digital value 128 to in-phase amplitude 124 sampling incoming signal 114 at substantially one-quarter of period 116 after incoming time 122 to produce a quadrature amplitude 132 of incoming signal 114, assigning a quadrature digital value 136 to quadrature amplitude 132, calculating a magnitude 140 at incoming time 122 based on in-phase digital value 128 and quadrature digital value 136, calculating a phase 144 at incoming time 122 based on in-phase digital value 128 and quadrature digital value 136, measuring a difference 148 between outgoing amplitude 106 and magnitude 140, applying a first illumination 150-1 to an image point 154 in substantial proportion to difference 148, and applying a second illumination 150-2 to image point 154 in substantial proportion to phase 144.

In one embodiment, the method of beam-forming for ultrasound imaging may further include the steps of transducing outgoing signal 104 to second outgoing ultrasound 112-2, receiving at least a portion of reflected outgoing ultrasound 112 and second outgoing ultrasound 112-2, transducing reflected outgoing ultrasound 112 and second outgoing ultrasound 112-2 to a second incoming signal 114-2 having a second period 116-2, sampling second incoming signal 114-2 at incoming time 122 to produce a second in-phase amplitude 124-2 of second incoming signal 114-2, assigning a second in-phase digital value 128-2 to second in-phase amplitude 124-2, sampling second incoming signal 114-2 at substantially one-quarter of second period 116-2 after incoming time 122 to produce a second quadrature amplitude 122-2 of second incoming signal 114-2, assigning a second quadrature digital value 136-2 to second quadrature amplitude 122-2, calculating a second magnitude 140-2 at incoming time 122 based on second in-phase digital value 128-2 and second quadrature digital value 136-2, calculating a second phase 144-2 at incoming time 122 based on second in-phase digital value 128-2 and second quadrature digital value 136-2, measuring a second difference 148-2 between outgoing amplitude 106 and second magnitude 140-2, summing difference 148, second difference 148-2, phase 144, and second phase 144-2, applying a third illumination 150-3 to image point 154 in substantial proportion to second difference 148-2, and applying a fourth illumination 150-4 to image point 154 in substantial proportion to second phase 144-2.

In one embodiment, the method of beam-forming may be repeated to produce a plurality of image points 154 forming an image 168. In several embodiments, image 168 may be viewed, used to guide insertion of a needle, used to guide insertion of a catheter, used to guide insertion of an endoscope, used to estimate blood flow, or used to estimate tissue motion. In one embodiment, plurality of image points 154 may be focused. In one embodiment, focusing may be repeated on reflected outgoing ultrasound 112 at plurality of image points 154.

In one embodiment, plurality of image points 154 may be along a line at a range of interest. In one embodiment, a line may be formed at a plurality of ranges to form a planar image. In one embodiment, the planar image may be a B-mode image. In one embodiment, plurality of image points 154 may lie within a plane at a range of interest. In one embodiment, plurality of image points 154 may form a C-scan. In one embodiment, the plane may be formed at multiple ranges. In one embodiment, several planes may form a complex 1-D image. In one embodiment, sampling is performed at several ranges for one transmit event to thereby increasing the image formation rate.

In one embodiment, an envelope of magnitude 140 may be displayed. In one embodiment, phase 144 may be used to compensate for a path difference 148 between various transducers and object 170. In one embodiment, a main lobe resolution and a side lobe level may be balanced based on magnitude 140. In one embodiment, a sum squared error between a desired system response and a true system response may be minimized.

One skilled in the art would appreciate that a variety of tissue information may be obtained through judicious pulse transmission and signal processing of received echoes with the current invention. Such information could be displayed in conjunction with or instead of the aforementioned echo information.

One such type of information is referred to as color flow Doppler as described in U.S. Pat. No. 4,573,477 to Namekawa et al., entitled "Ultrasonic Diagnostic Apparatus," hereby incorporated by reference herein in its entirety. Another useful type of information is harmonic image data as described in U.S. Pat. No. 6,251,074 to Averkiou et al., entitled "Ultrasonic Tissue Harmonic Imaging" and U.S. Pat. No. 5,632,277 to Chapman et al., entitled "Ultrasound Imaging System Employing Phase Inversion Subtraction to Enhance the Image," both of which are hereby incorporated by reference herein in their entirety. Yet another type of information that may be obtained and displayed is known as Power Doppler as described in U.S. Pat. No. 5,471,990 to Thirsk, entitled "Ultrasonic Doppler Power Measurement and Display System," hereby incorporated by reference herein in its entirety.

Angular scatter information might also be acquired using a method described in a co-pending U.S. patent application Ser. No. 10/030,958, entitled "Angular Scatter Imaging System Using Translating Apertures Algorithm and Method Thereof," filed Jun. 3, 2002, of which is hereby incorporated by reference herein in its entirety. Speckle is a common feature of ultrasound images. While it is fundamental to the imaging process, many users find its appearance confusing and it has been shown to limit target detectability. A variety of so called compounding techniques have been described which could be valuable for reducing the appearance of speckle in ultrasound transducer drive images. These techniques include spatial compounding and frequency compounding, both of which are well described in the literature.

One skilled in the art would appreciate that the common practice of frequency compounding could be readily applied to the current invention. By transmitting a plurality of pulses at different frequencies and forming separate detected images using the pulses one may obtain multiple unique speckle patterns from the same target. These patterns may then be averaged to reduce the overall appearance of speckle.

The well known techniques of spatial compounding may also be applied to the current invention. The most conventional form of spatial compounding, which we call two-way or transmit-receive spatial compounding, entails the acquisition of multiple images, multiple looks, with the active transmit and receive apertures shifted spatially between image acquisitions. This shifting operation causes the speckle patterns obtained to differ from one image to the next, enabling image averaging to reduce the speckle pattern.

In another technique, which we term one-way or receive-only spatial compounding, the transmit aperture is held constant between image acquisitions while the receive aperture is shifted between image acquisitions. As with two-way spatial compounding, this technique reduces the appearance of speckle in the final image.

In many ultrasound applications the received echoes from tissue have very small amplitude, resulting in an image with poor signal to noise ratio. This problem may be addressed through the use of a technique known as coded excitation. In this method the transmitted pulse is long in time and designed so that it has a very short auto-correlation length. In this manner the pulse is transmitted and received signals are correlated with the transmitted pulse to yield a resultant signal with good signal to noise ratio, but high axial resolution (short correlation length). This method could be readily applied in the present invention ultrasound transducer drive device and method to improve the effective signal to noise ratio. The coded excitation technique is described in U.S. Pat. No. 5,014,712 to O'Donnell, entitled "Coded Excitation for Transmission Dynamic Focusing of Vibratory Energy Beam," hereby incorporated by reference herein in its entirety.

An aspect in fabricating a system like the present invention ultrasound imaging beam-forming apparatus is in construction of the transducer array. Both cost and complexity could be reduced by incorporating a transducer implemented using photolithographic techniques, i. e. the transducer is formed using micro electro mechanical systems (MEMS). One particularly attractive approach has been described in U.S. Pat. No. 6,262,946 to Khuri-Yakub et al., entitled "Capacitive Micromachined Ultrasonic Transducer Arrays with Reduced Cross-Coupling," hereby incorporated by reference herein in its entirety.

While the present invention may be embodied in many different forms, a number of illustrative embodiments are described herein with the understanding that the present disclosure is to be considered as providing examples of the principles of the invention and such examples are not intended to limit the invention to preferred embodiments described herein and/or illustrated herein.

BROAD SCOPE OF THE INVENTION

While illustrative embodiments of the invention have been described herein, the present invention is not limited to the various preferred embodiments described herein, but includes any and all embodiments having equivalent elements, modifications, omissions, combinations (e. g., of aspects across various embodiments), adaptations and/or alterations as would be appreciated by those in the art based on the present disclosure. The limitations in the claims are to be interpreted broadly based on the language employed in the claims and not limited to examples described in the present specification or during the prosecution of the application, which examples are to be construed as non-exclusive. For example, in the present disclosure, the term "preferably" is non-exclusive and means "preferably, but not limited to." In this disclosure and during the prosecution of this application, means-plus-function or step-plus-function limitations will only be employed where for a specific claim limitation all of the following conditions are present in that limitation: a) "means for" or "step for" is expressly recited; b) a corresponding function is expressly recited; and c) structure, material or acts that support that structure are not recited. In this disclosure and during the prosecution of this application, the terminology "present invention" or "invention" may be used as a reference to one or more aspect within the present disclosure. The language present invention or invention should not be improperly interpreted as an identification of criticality, should not be improperly interpreted as applying across all aspects or embodiments (i. e., it should be understood that the present invention has a number of aspects and embodiments), and should not be improperly interpreted as limiting the scope of the application or claims. In this disclosure and during the prosecution of this application, the terminology "embodiment" can be used to describe any aspect, feature, process or step, any combination thereof, and/or any portion thereof, etc. In some examples, various embodiments may include overlapping features. In this disclosure, the following abbreviated terminology may be employed: "e.g." which means "for example;" and "NB" which means "note well."

What is claimed is:

1. An apparatus, comprising:
a transducer array, comprising a plurality of transducers, each configured to convert reflected ultrasound pulses to at least one incoming signal, wherein each of the at least one incoming signals has a period and an amplitude;
a signal receiver comprising:
a first sample-and-hold circuit configured to sample a first amplitude of the at least one incoming signal from a transducer at a first specified instant, the first sample-and-hold circuit configured to acquire at most one amplitude sample per an ultrasound transmit pulse/receive acquisition cycle, the first sample representing an in-phase amplitude;
a separate second sample-and-hold circuit configured to sample a second amplitude of the at least one incoming signal from the transducer at a second specified instant, the second specified instant offset in time from the first specified instant by an amount less than about half the period of the incoming signal, the second sample-and-hold circuit configured to acquire at most one amplitude sample per the ultrasound transmit pulse/receive acquisition cycle, the second sample representing a quadrature amplitude;
at least one analog-to-digital converter configured to convert the sampled amplitudes to digital values after both of the first and second sample-and-hold circuits have completed sampling; and
a focusing apparatus configured to combine the digital values and to generate at least one image point.

2. The apparatus of claim 1 wherein only a subset of the plurality of transducers are used to convert reflected ultrasound.

3. The apparatus of claim 1 further comprising a transmit array having a first subset of transducer elements and a receive array comprising a second subset of elements, and the first subset and second subsets are not identical.

4. The apparatus of claim 3 wherein the second subset of elements is chosen to minimize speckle distortion.

5. The apparatus of claim 1 further comprising a transmit array having a first subset of transducer elements and a receive array comprising a second subset of elements, and the first subset and second subsets are identical.

6. The apparatus of claim 1 wherein the focusing apparatus is further configured to provide a phase rotation.

7. The apparatus of claim 1 wherein the second sample-and-hold circuit is triggered one-quarter of the period after the first sample-and-hold circuit is triggered.

8. The apparatus of claim 1 wherein the at least one analog-to-digital converter comprises:
a ramp generator configured to provide a digitization signal;
a comparator configured to:
compare the digitization signal to an input of the respective analog-to-digital converter; and
output a digital value; and
a latch configured to:
receive the digital value; and
provide an output equal the digital value when a clock signal is applied to the latch.

9. The apparatus of claim 6 wherein the at least one analog-to-digital converter includes an analog-to-digital converter configured to receive the in-phase amplitude and output the first digital value representative of the in-phase amplitude and receive the quadrature amplitude and output the second digital value representative of the quadrature amplitude.

10. The apparatus of claim 1 comprising:
a magnitude calculator configured to receive the digital values and responsively generate a magnitude; and
a phase calculator configured to receive the digital values and responsively generate a phase.

11. The apparatus of claim 1 wherein a protection circuit switches between a transmit mode and a receive mode, allowing the transducer to both transmit and receive ultrasound.

12. A method, comprising:
using a plurality of transducers to receive reflected ultrasound signals, each transducer generating a respective incoming signal having a period and an amplitude;
obtaining a pair of digital values for each respective incoming signal by:
sampling a first amplitude of the respective incoming signal from a transducer at a first specified instant with an in-phase sample-and-hold circuit to create an in-phase sample, where the in-phase sample-and-hold circuit acquires at most one amplitude sample per an ultrasound transmit pulse/receive acquisition cycle;
sampling the amplitude of the respective incoming signal from the transducer at a second specified instant with a separate quadrature sample-and-hold circuit to create a quadrature sample, the second specified instant offset in time from the first specified instant by less than about half the period of the respective incoming signal, where the quadrature sample-and-hold acquires at most one amplitude sample per the ultrasound transmit pulse/receive acquisition cycle; and
after both the in-phase and quadrature sample-and-hold circuits have completed sampling, digitizing each of the in-phase and the quadrature samples to obtain the pair of digital values; and processing the pair of digital values for each respective incoming signal to obtain at least one focused image point.

13. The method of claim 12 wherein the amount less than one period of the incoming signal is one quarter of the period.

14. The method of claim 12 wherein a plurality of analog-to-digital converters obtain the in-phase amplitude sample and the quadrature amplitude sample and assigns an in-phase digital value to the in-phase amplitude sample, and assigns a quadrature digital value to the quadrature amplitude sample.

15. The method of claim 12 wherein processing the pair of digital values comprises applying complex weights to the pair of digital values to focus the image point.

16. The method of claim 12 wherein processing the pair of digital values comprises:
    calculating a magnitude based on the in-phase digital value and the quadrature digital value; and
    calculating a phase based on the in-phase digital value and the quadrature digital value.

17. The method of claim 12 wherein the least one focused image point forms an image having a format selected from the group consisting of:
    a planar image;
    B-mode image;
    C-scan image;
    3-D image data;
    and a complex 1-D image.

18. The method of claim 16 further comprising displaying an envelope of the magnitude.

19. The method of claim 16 further comprising applying an illumination to an image point substantially in proportion to the phase.

20. The method of claim 16 further comprising compensating for a path difference with the phase.

21. The method of claim 16 further comprising balancing a main lobe resolution and a side lobe level based on the magnitude.

22. The method of claim 12 wherein processing a plurality of signal pairs to obtain at least one focused image point comprises applying calculated phase delays to the plurality of signal pairs.

23. An apparatus, comprising:
    a transducer array comprising multiple transducer elements, wherein each transducer element is configured to convert reflected ultrasound pulses to a respective incoming signal, the incoming signal having a period and an amplitude;
    a sampling clock configured to generate trigger signals to initiate sampling;
    an in-phase sample-and-hold circuit configured to sample the amplitude of the respective incoming signal at a first trigger signal to create and in-phase sample, the sampling clock configured to generate the first trigger signal at most once per an ultrasound transmit pulse/receive acquisition cycle;
    a separate quadrature sample-and-hold circuit configured to sample the amplitude of the respective incoming signal at a second trigger signal to create a quadrature sample, the second trigger signal offset in time from the first trigger signal by less than about half the period of the incoming signal, the sampling clock configured to generate the second trigger signal at most once per an ultrasound transmit pulse/receive acquisition cycle;
    an analog-to-digital converter configured to digitize each of the in-phase sample and the quadrature sample to obtain a pair of digital values after both of the first and second sample-and-hold circuits have completed sampling; and
    a focusing apparatus configured to generate an image point based on the pair of digital values.

24. The apparatus of claim 23 wherein the transducer array comprises a transmit array and a receive array, wherein the transmit array comprises a first subset of elements and the receive array comprises a second subset of elements, and the first and second subsets are not identical.

25. The apparatus of claim 24 wherein the second subset of elements is chosen to minimize speckle distortion.

26. The apparatus of claim 23 wherein the transducer array comprises a transmit array and a receive array, wherein the transmit array comprises a first subset of elements and the receive array comprises a second subset of elements, and the first and second subsets are identical.

27. The apparatus of claim 23 wherein the focusing apparatus is further configured to provide a phase rotation.

28. The apparatus of claim 23 comprising:
    a magnitude calculator configured to receive an in-phase digital value and a quadrature digital value outputting and output a magnitude;
    a phase calculator configured to receive the in-phase digital value and the quadrature digital value outputting and output a phase.

29. The apparatus of claim 26 further comprising a protection circuit configured to switch between a transmit mode and a receive mode, thereby allowing the array to both transmit and receive ultrasound.

* * * * *